(12) United States Patent
Rose et al.

(10) Patent No.: US 7,499,760 B2
(45) Date of Patent: Mar. 3, 2009

(54) AUTOMATIC CONTROL FOR DENTAL APPLICATIONS

(75) Inventors: Eric P. Rose, Tarzana, CA (US); Robert Hayman, Los Angeles, CA (US); Bruce Sargeant, Orange, CA (US)

(73) Assignee: Discus Dental, LLC, Culver City, CA (US)

(*) Notice: Subject to any disclaimer, the term of this patent is extended or adjusted under 35 U.S.C. 154(b) by 516 days.

(21) Appl. No.: 11/174,363

(22) Filed: Jun. 30, 2005

(65) Prior Publication Data

US 2006/0029902 A1 Feb. 9, 2006

Related U.S. Application Data

(63) Continuation-in-part of application No. 29/232,670, filed on Jun. 22, 2005, now Pat. No. Des. 538,960, and a continuation-in-part of application No. 29/232,671, filed on Jun. 22, 2005, now Pat. No. Des. 539,956, and a continuation-in-part of application No. 29/220,642, filed on Jan. 4, 2005, now Pat. No. Des. 542,947, and a continuation-in-part of application No. 29/220,680, filed on Jan. 4, 2005, now Pat. No. Des. 537,192, and a continuation-in-part of application No. 29/220,679, filed on Jan. 4, 2005, now Pat. No. Des. 543,937, and a continuation-in-part of application No. 29/220,712, filed on Jan. 4, 2005, now Pat. No. Des. 538,459.

(60) Provisional application No. 60/585,224, filed on Jul. 2, 2004, provisional application No. 60/641,462, filed on Jan. 4, 2005, provisional application No. 60/647,725, filed on Jan. 26, 2005, provisional application No. 60/647,723, filed on Jan. 26, 2005, provisional application No. 60/658,517, filed on Mar. 3, 2005, provisional application No. 60/641,469, filed on Jan. 4, 2005, provisional application No. 60/647,580, filed on Jan. 26, 2005, provisional application No. 60/641,461, filed on Jan. 4, 2005, provisional application No. 60/641,468, filed on Jan. 4, 2005, provisional application No. 60/647,612, filed on Jan. 26, 2005, provisional application No. 60/647,593, filed on Jan. 26, 2005, provisional application No. 60/604,577, filed on Aug. 25, 2004, provisional application No. 60/594,297, filed on Mar. 25, 2005, provisional application No. 60/631,267, filed on Nov. 26, 2004, provisional application No. 60/594,327, filed on Mar. 30, 2005, provisional application No. 60/664,696, filed on Mar. 22, 2005.

(51) Int. Cl.
*G05B 15/00* (2006.01)
*A61C 1/00* (2006.01)
*A61C 5/00* (2006.01)
*A61C 15/00* (2006.01)
*A61B 1/32* (2006.01)

(52) U.S. Cl. .................. 700/1; 433/29; 433/215; 433/216; 600/205

(58) Field of Classification Search .................. 700/1; 433/29, 215, 216; 600/205
See application file for complete search history.

(56) References Cited

U.S. PATENT DOCUMENTS 3,916,880 A 11/1975 Schroer (Continued)

*Primary Examiner*—Albert DeCady
*Assistant Examiner*—Thomas H Stevens

(57) ABSTRACT

A dental lamp includes a control system adapted to control operation of a light source within the dental lamp. The control system requires that an unexpended light guide including a recordable medium be coupled to a lamp head of the dental lamp, in order to illuminate the light source. The control system records a first data signal on the recordable medium during illumination of the light source indicating that the light guide has been expended. The control system also records a second data signal onto a second recordable medium so that a particular duration of use of the light source may be indicated.

25 Claims, 13 Drawing Sheets

U.S. PATENT DOCUMENTS

| | | | |
|---|---|---|---|
| 5,637,863 A * | 6/1997 | Sanborn et al. | 250/221 |
| 6,089,740 A * | 7/2000 | Forehand et al. | 362/573 |
| 6,193,510 B1 | 2/2001 | Tsimerman | |
| 6,733,290 B2 | 5/2004 | West et al. | |
| 2004/0076926 A1 | 4/2004 | Baughman | |

* cited by examiner

US 7,499,760 B2

AUTOMATIC CONTROL FOR DENTAL APPLICATIONS

CROSS-REFERENCE TO RELATED APPLICATIONS

This application claims the benefit of U.S. provisional patent application Ser. No. 60/585,224, filed Jul. 2, 2004, entitled "Dental Light Devices With Phase Change Heat Sink"; 60/641,462, filed Jan. 4, 2005, entitled "Boom Hinge For A Dental Lamp"; 60/647,725, filed Jan. 26, 2005, entitled "Automatic Control for a Dental Whitening Lamp"; 60/647,723, filed Jan. 26, 2005, entitled "Boom Hinge For A Dental Lamp"; 60/658,517, filed Mar. 3, 2005, entitled "Apparatus and Method For Radiation Spectrum Shifting in Dentistry Applications"; 60/641,469, filed Jan. 4, 2005, entitled "Lamp For Dentistry Applications"; 60/647,580, filed Jan. 26, 2005, entitled "Light Guide For Dental Whitening Lamp"; 60/641,461, filed Jan. 4, 2005, entitled "Support Structure For A Dental Lamp"; 60/641,468, filed Jan. 4, 2005, entitled "Light Guide For A Dental Whitening Lamp"; 60/647,612, filed Jan. 26, 2005, entitled "Light Path Apparatus For A Dental Lamp"; 60/647,593, filed Jan. 26, 2005, entitled "Support Structure For A Dental Lamp"; 60/604,577, filed Aug. 25, 2004, entitled "Lip Retractors"; 60/594,297, filed Mar. 25, 2005, entitled "Curing Light Having A Detachable Tip"; 60/631,267, filed Nov. 26, 2004, entitled "Curing Light Having A Reflector"; 60/594,327, filed on Mar. 30, 2005, entitled, "Curing Light"; and 60/664,696, filed Mar. 22, 2005, entitled "Curing Light Having A Detachable Tip"; the contents of all of which are hereby incorporated by reference.

The current application is a continuation-in-part of the following U.S. design patent applications Ser. No.: 29/220,642, filed Jan. 4, 2005, entitled "Lamp For Dentistry Applications", now granted as D542,947; 29/220,680, filed Jan. 4, 2005, entitled "Light Guide For Dentistry Applications", now granted as D537,192; 29/220,679, filed Jan. 4, 2005, entitled "Power Pack For Dentistry Applications", now granted as D543,937; 29/220,712, filed Jan. 4, 2005, entitled "Support Structure For A Lamp For Dentistry", now granted as D538,459; 29/232,670 filed on Jun. 22, 2005 entitled, "Support Structure For Dental Applications, " now granted as D538,960; 29/232,671 filed on Jun. 22, 2005 entitled, "Support Structure For Dental Applications", now granted as D539,956; all of which are incorporated herein by reference.

The present application includes claims that may be related to the claims of U.S. patent application Ser. No. 11/173,371, concurrently filed on Jun. 30, 2005, entitled "Support System for Dentistry Equipment"; and U.S. patent application Ser. No. 11/173,709, entitled, "Voice Alert in Dentistry" concurrently filed on Jun. 30, 2005, now abandoned; the contents of which are hereby incorporated by reference.

FIELD OF THE INVENTION

This invention relates to dental applications. Specifically, this invention relates to control mechanisms in dental applications.

BACKGROUND OF THE INVENTION

A tooth is comprised of an inner dentin layer and an outer hard enamel that is coated with a protective layer called the acquired pellicle. The enamel layer is composed of hydroxyapatite crystals that create a somewhat porous surface. The pellicle or the enamel can become stained or discolored. It is believed that the porous nature of the enamel layer is what allows staining agents and discoloring substances to permeate the enamel and discolor the tooth.

Tooth discoloration has a number of causes. For example, the teeth may become stained by coffee or tea drinking, or by the use of tobacco products, or by drinking water with a high mineral content.

One solution to the staining problem is through tooth bleaching. Some dentifrices, like toothpastes, gels, and powders, contain active oxygen or hydrogen peroxide liberating bleaching agents including peroxides, percarbonates and perborates of the alkali and alkaline earth metals or complex compounds containing hydrogen peroxide.

Dental bleaching can be done either in a dental office or at home. Bleaching in a dental office generally employs compositions activatable with the aid of light sources having the appropriate wavelength outputs in order to speed up the process. Additionally, the bleaching compositions used in a dental office typically contain a higher percentage concentration of bleaching agents than the bleaching compositions found in home applications.

In addition to staining, tooth decay, resulting in cavities or other damages can also result. In the field of tooth restoration and repair, dental cavities are often filled and/or sealed with compounds that are photosensitive, either to visible and/or ultraviolet light. These compounds, commonly known as light-curable compounds, are placed within dental cavity preparations or onto dental surfaces and are cured when exposed to light from a dental curing light device.

Unlike dental curing processes, which are generally relatively fast processes, dental bleaching takes a much longer time, sometimes amounting to more than an hour per office visit. In addition, dental restoration is often an unwelcome experience. Therefore, it is advantageous that a person undergoing the processes, either dental restoration or bleaching, be as comfortable as possible.

The process is generally performed in a dentist's chair. Typically a dentist's chair has a wide range of adjustability such that a patient may be placed in a wide range of positions from a nearly full reclining position to a nearly upright position. In order to effectively accomplish the whitening or restoration process, a light source needs to be aligned with the mouth. The wide range of dentist's chair positions can make this alignment difficult.

Further considerations in the process of dental procedures include the ability to maintain cleanliness of the light source, and particularly of any part that comes into contact with the patient. Further, the process of whitening is preferably optimized, that is, the light source is on as long as necessary to whiten the teeth to the desired degree. Still further, it is preferable that the light source be as efficient as possible. An efficient lamp tends to be cooler and therefore safer than an inefficient lamp. Also, an efficient lamp requires less energy to run than an inefficient lamp.

It remains desirable to have an efficient and comfortable apparatus and method for dental whitening.

SUMMARY OF THE INVENTION

The present invention is directed to an apparatus and method for controlling a dental whitening and curing process. The control apparatus and method are adapted to produce dental whitening or curing that is efficient, comfortable for the patient with improved safety, maintenance and operating features.

In dental whitening, cleaning and/or bleaching agents are applied to the teeth of a patient. In tooth repair or restoration, composite filling materials are applied to surface and/or cavity in a tooth. The bleaching agents and/or composite materials are activated by the application of energy, such as, for example electromagnetic energy.

In order to achieve effective activation of dental whitening compounds and effective curing of dental composite materials, the whitening compounds and/or composite materials may be illuminated with light of an appropriate intensity and wavelength, for an appropriate duration, so as to receive the an overall desired energy level. Also, because light wavelengths that are most effective for chemical activation of a dental whitening compound or curing composite may be deleterious to soft tissues, it is desirable to minimize the exposure of a patient's gums, tongue, facial skin and other soft tissues to the light source. Therefore, properly controlling the duration and intensity of the applied light is desirable in dental whitening and curing applications.

The present invention includes a dental whitening or curing light source having a control system for indicating the duration of light application.

Moreover, since light intensity varies as the inverse cube of distance from a light source, it is important that the light source used to activate a whitening compound or restorative composite be in reasonably close proximity to the tooth surfaces being treated. In order to achieve desirable positioning of a target tooth with respect to the light source, it is desirable to employ a fixturing device. In one aspect, the fixturing device may include a spacer, such as a light guide, and/or a reference device such as a lip retracting device. The light guide is a substantially tubular member adapted to couple at a first end to a lamp housing, and at a second end to the lip retracting device. The lip retracting device may be adapted to couple to the lips of a patient, so as to hold the patient's head and teeth in a substantially fixed relation to the light guide, and therefore to the lamp housing.

In order to insure hygienic conditions for every patient, according to one aspect of the invention, the lip retractor and light guide may be constructed to be single-use items, to be disposed of after use by a single patient. To aid the dental professional in monitoring the use, according to one embodiment of the invention, the dental lamp system includes a control system adapted to prevent reuse of the fixturing device.

According to a particular embodiment of the invention, the control system includes a recordable medium coupled to the light guide. In another aspect of the invention, the control mechanism may operate in a manner that the inhibition against re-use occurs during the attachment process of the light guide to the lamp system. In a further aspect, the control mechanism may operate to inhibit the lamp from being turned on if the light guide has been previously used.

According to another embodiment, the invention includes a reflector having an axial cavity with a first aperture at an end proximate the light source and a second aperture distal to the light source. The second reflector includes a reflective internal surface adapted to direct light from the light source towards the second aperture by reflection.

According to one embodiment of the invention, the housing includes at least one formation in proximity to the front aperture. The formation serves as a mechanical coupling feature, according to one embodiment of the invention, to provide a secure, removable connection between the housing and a light guide.

According to various embodiments of the invention, the light guide includes a tubular inner surface that is disposed about an axial cavity that may be filled with ambient air. An aperture at a proximal end of the light guide may be adapted for positioning adjacent to the front aperture of the lamp housing. A further aperture exists at a distal end of the light guide. The light guide includes at least one formation adapted to interface with the formation of the housing. In one embodiment of the light guide, the light guide includes air vents for patient breathing comfort during the bleaching or curing treatment.

The material of the light guide is chosen to absorb and/or reflect light of one or more ranges of wavelength that impinges on the tubular inner surface. Consequently, according to one aspect of the invention, the light guide reduces the degree to which light escapes from the system except through the distal aperture of the light guide.

In one embodiment of the invention, the light guide includes a second formation adapted to removably couple the light guide to a reference device for positioning the light guide, and consequently the lamp head and the light source, in a substantially constant position and orientation with respect to a target.

In one embodiment of the invention, the reference device is a fixturing device including a lip retracting device having geometric features adapted to receive one or more lips of a patient in a tooth restoration or whitening process.

One embodiment of the invention effects control of light guide usage by including a recording medium in the light guide and a signal generating device elsewhere in the lamp system. In one aspect, the invention includes receipt by the recording medium of a signal from the signal generating device. The invention further includes a method for recording a record on the recording medium. The record corresponds to the received signal and produces a substantially permanent signal record. In another aspect of the invention, the substantially permanent signal record is read by a medium reading device and a condition of use of the particular light guide containing the recording medium is ascertained. Based on the condition of use indicated by the record, as read, a control device external to the light guide serves to allow or inhibit activation of the light source.

In one embodiment of the invention, the signal generating and record reading devices are located within the lamp housing. In another embodiment of the invention, one or more of the signal generating and record reading devices are located external to the lamp head housing.

In one embodiment of the invention, the signal from the signal generating source is received at the recording medium by way of an electromechanical coupling. In another embodiment of the invention, the signal from the signal generating source is received at the recording medium by way of an optical communication channel. In a still further embodiment of the invention, the signal from the signal generating source is received at the recording medium by way of a mechanical communication channel, an acoustic communication channel, a radiofrequency communication channel, or any other communication medium appropriate the particular invention embodiment.

In one embodiment of the invention, the control system includes a microcontroller or microprocessor device. A microcontroller is a specialized microprocessor adapted to control use in embedded control applications. According to one embodiment of the invention, the microcontroller employed is an Intel MCS 8051 microcontroller, which is well-known in the art.

In one embodiment of the invention, the Intel MCS 8051 microcontroller is disposed on a printed circuit board within a power pack module. In one embodiment, the power pack module includes, in addition to the MCS 8051 microcontroller, a power supply adapted to receive a line voltage of, for example, 120 volts and provide at least one operating voltage and appropriate to control of an Intel MCS 8051 microcontroller.

The present invention together with the above and other advantages may best be understood from the following detailed description of the embodiments of the invention illustrated in the drawings, wherein:

DETAILED DESCRIPTION OF THE INVENTION

Figure 1:
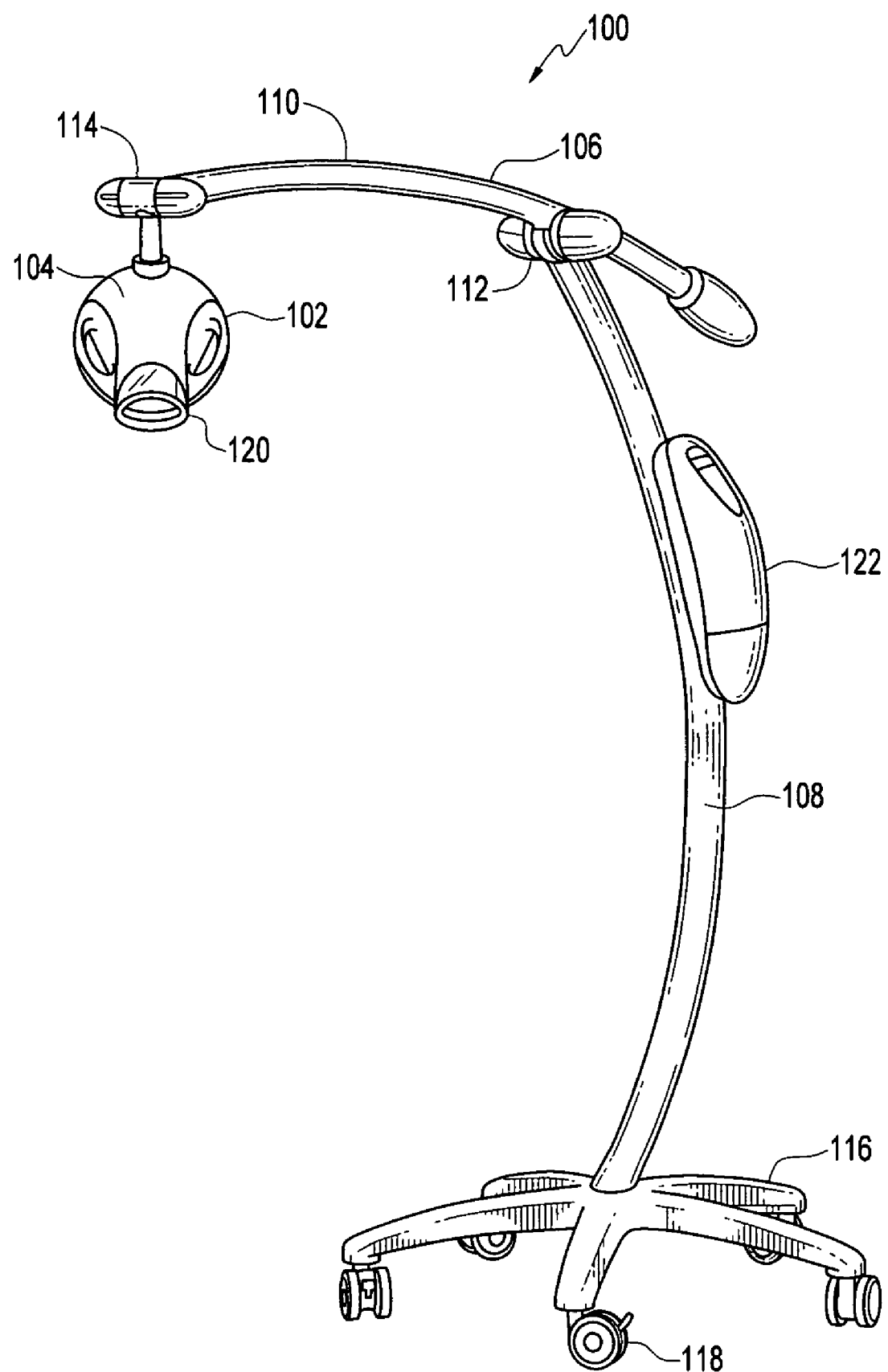
FIG. 1 shows, in perspective view, a lamp for dentistry procedures including a control system according to one embodiment of the invention.

The detailed description set forth below is intended as a description of the presently exemplified tooth bleaching and dental material curing methods and apparatus provided in accordance with aspects of the present invention and is not intended to represent the only forms in which the present invention may be prepared or utilized. The description sets forth the features and the steps for preparing and using the tooth bleaching and dental material curing methods and apparatus of the present invention. It is to be understood, however, that the same or equivalent functions and components incorporated in the tooth bleaching and dental curing methods and apparatus may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present to invention relates to a system and method for controlling a lamp for dentistry applications. In various embodiments, the invention includes dental whitening lamps, dental curing lamps, and other illumination sources for dentistry applications and related control systems. The various dental lamps and control systems of the present invention are adapted to be used in both the dental examining room and in other clinical and non-clinical applications, such as in a dental laboratory.

The control system and method of the present invention are adapted to produce, for example, in addition to dental whitening and curing, comfort for the patient, and to further improve safety, maintainability, and ease of operation of a dental illumination source with which it is employed. In a further aspect, the control system and method of the present invention are adapted to produce curing of a dental composite that is efficient, and complete, and may be performed in an optimal duration.

For example, in the practice of dental whitening, cleaning and/or bleaching agents are applied to a tooth. The application of electromagnetic radiation, such as infrared radiation or ultraviolet radiation may be used to effect bleaching.

In the practice of other dental procedures, such as the filling of caries, dental adhesives and cements are applied to a prepared surface of a tooth. As in the case of dental whitening, the application of electromagnetic energy such as visible light or ultraviolet light may be used to stimulate curing of the adhesives, composites and cements.

In These exemplary activities, as in other light activatable dentistry processes, the efficacy of the procedure may be related to the intensity and duration of the applied illumination. In particular, the application of light for an insufficient duration may result in a tooth brightness that is less white that might otherwise be achieved, or a chemical cure that is less than complete.

At the same time, because the wavelengths most effective for chemical activation of a dental whitening compound or other dental composition may be deleterious to soft tissues, as mentioned above, properly controlling the duration and intensity of the applied light to known tolerances so as to produce optimal results is desirable.

In addition, in order to produce predictable, and therefore optimizable results, it is important that the intensity of the illumination received at a target position be substantially spatially and temporally controlled. Also, the above-noted desirability of limiting light exposure to the target composition motivates a further aspect of the invention in relation to fixturing of the light source and target area.

In order to effect uniform application of light to a target composition, and to prevent the undue exposure of non-target areas to illumination, the present invention includes, in various embodiments, a light-guide system.

According to one embodiment of the invention, and as will be described in further detail below, the light guide includes a tubular member having at least one formation adapted to be coupled at one end to at least one formation of an illumination source, and at least a second formation at an opposite end to at least one formation of a reference device, such as a lip retracting device, and thereby, to a patient. The effect of these respective couplings is to substantially fix a target dental region in a particular spatial relationship with respect to a light source.

In order to ensure hygienic conditions for every patient, according to one embodiment of the invention, the lip retracting device and light guide are prepared as single-used items. According to one embodiment of the invention, the dental lab system includes a control system adapted, for example, to inhibit reuse of the light guide.

According to one embodiment of the present invention, control system for controlling a duration of illumination of a dental lamp. The control system further controls a duration of use of ancillary components of dental lamps including, for example, a light guide.

The word formation as used herein in relation to the reference device, spacer, the lamp system and a support system refers to the portion of the reference device, spacer and lamp system which is shaped to inter-fit with a corresponding part of an adjoining component. It includes portions of the above listed article which are shaped by molding, or portions which are formed separately and then subsequently assembled.

Suitable inter-engaging formations include tongues and grooves, posts and sockets, swingable hooks and sockets, resilient clips and sockets, tongue or wing-like members and slots, ball and cavity, ball and socket, some of which are more specifically exemplified in detail below.

FIG. 1 shows, according to one embodiment of the invention, a lamp for dental procedures 100. As illustrated, the lamp 100 includes a lamp head 102 having a housing 104 and an illumination source disposed therein. The lamp head 102 is supported by a support structure 106.

In the illustrated embodiment, the support structure 106 includes an articulated member having a mast 108 and a boom 110 pivotally coupled to one another by a boom joint 112. According to one embodiment of the invention, the boom joint 112 is adapted to provide two degrees of freedom including, for example, angular motion in a horizontal plane and angular motion in a vertical plane.

In the illustrated embodiment, additional degrees of freedom are provided by a ball and socket joint 114 disposed between the lamp head 102 and the mast 110. Additional freedom to position the lamp head 102 in space in relation to a target is provided, according to one embodiment of the invention, by a mobile base 116. In one aspect of the illustrated embodiment, this mobile base 116 includes a plurality of casters 118 for mobility.

Individually or in combination, the boom joint 112, the ball and socket joint 114 and the mobile base 116 enhance the ability of a user to position the illumination source within the lamp head 102 in an optimal position for activation of a target composition. In addition, according to various embodiments of the invention, the boom joint 112, the ball and socket joint 114 and the mobile base 116 include respective detent features adapted to hold the boom joint 112, the ball and socket joint 114, and the mobile base 116 in respective substantially fixed positions so that a desired spatial position and orientation of the lamp head 102 may be maintained once it has been achieved.

According to one aspect of the invention, the housing 104 of the lamp head 102 includes a formation adapted to removably couple a light guide 120 to the housing 104 of the lamp head 102, as described above.

In one exemplary embodiment, a lip retracting device, may be coupled to a light guide that is in turn coupled to the lamp head 102. Consequently, it is important that the lamp head 102 be supported in a way that allows its position to be extensively adjusted, so that the lamp head 102 may be properly aligned with the patient for the dental operation. This alignment will remain during the operation, even allowing for slight movement of the patient's head. This is possible because the retracting device is removably engaged with the light guide 120, and is positioned but not fixed to allow for this slight movement of the patient's head.

According to a further aspect of the invention, a further housing, referred to in an exemplary embodiment as a power pack 122 is coupled to, and supported by, the mast 108. In various embodiments of the invention, as will be discussed in further detail below, the power pack 122 includes power supply features, control features, and user interface features. Also in various embodiments of the invention, as will be discussed in further detail below, the lamp 100 includes a power supply cable coupled to the power pack 122, and signal and power cables coupled between the power pack 122 and the lamp head 102.

Figure 1A:
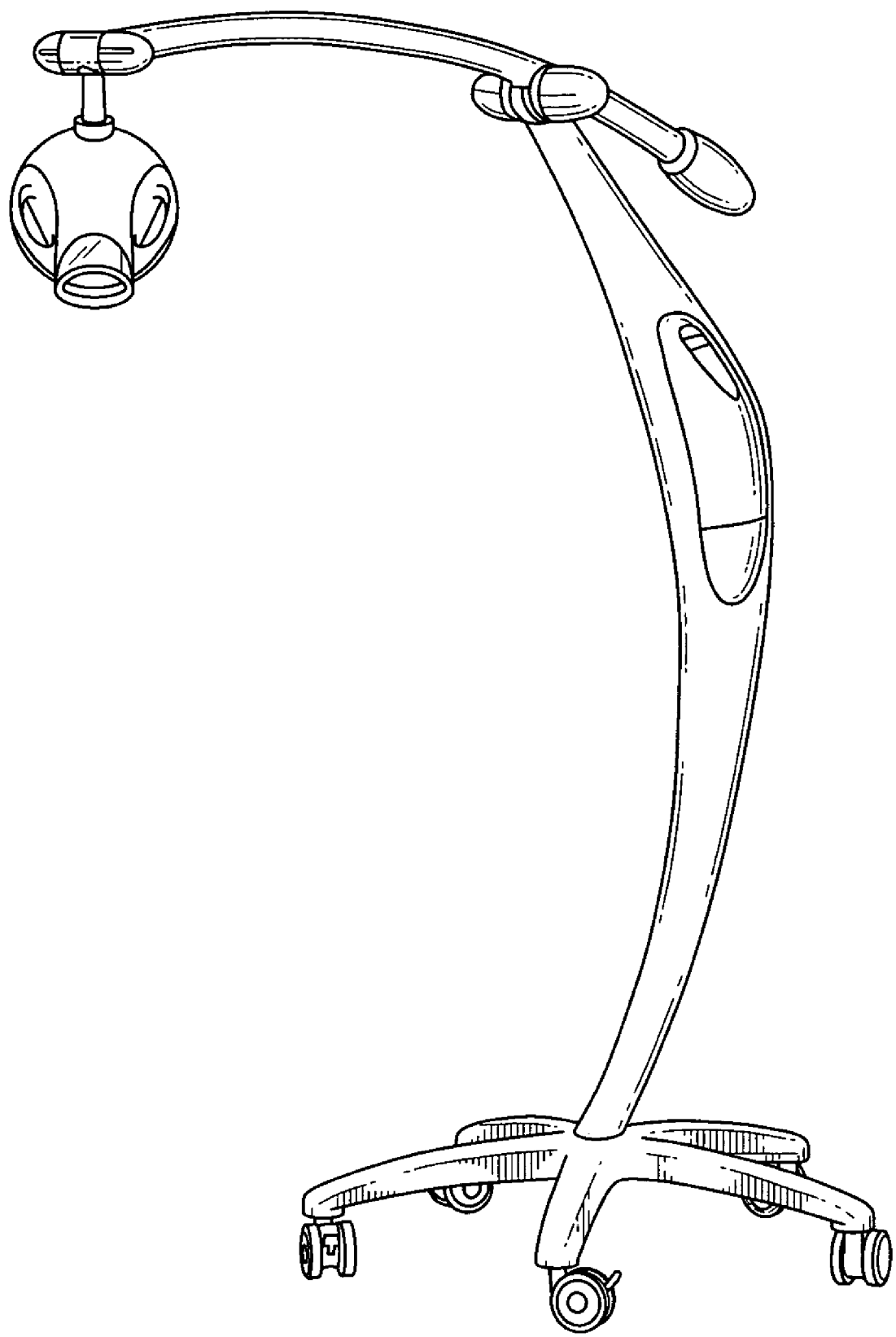
FIG. 1a shows, in perspective view, another embodiment of FIG. 1 according to the invention.

In one embodiment, the mast 110 may have a uniform outer dimension along its length, as shown in FIG. 1. In another embodiment, the mast 110 may have a non-uniform outer dimension along its length, as shown in FIG. 1a. In FIG. 1a, the mid-section of the mast 110 is of a larger dimension than other parts of the mast. In one aspect, this mid-section may coincide with the mounting position of the power pack 122. In another aspect, the wider portion of the mast 110 may be flattened to accommodate a power pack 122. In a third aspect, the wider portion may be sunken or recessed to accommodate a power pack 122 so that the power pack 122 does not protrude far from the general profile of the mast 110.

Figure 2:
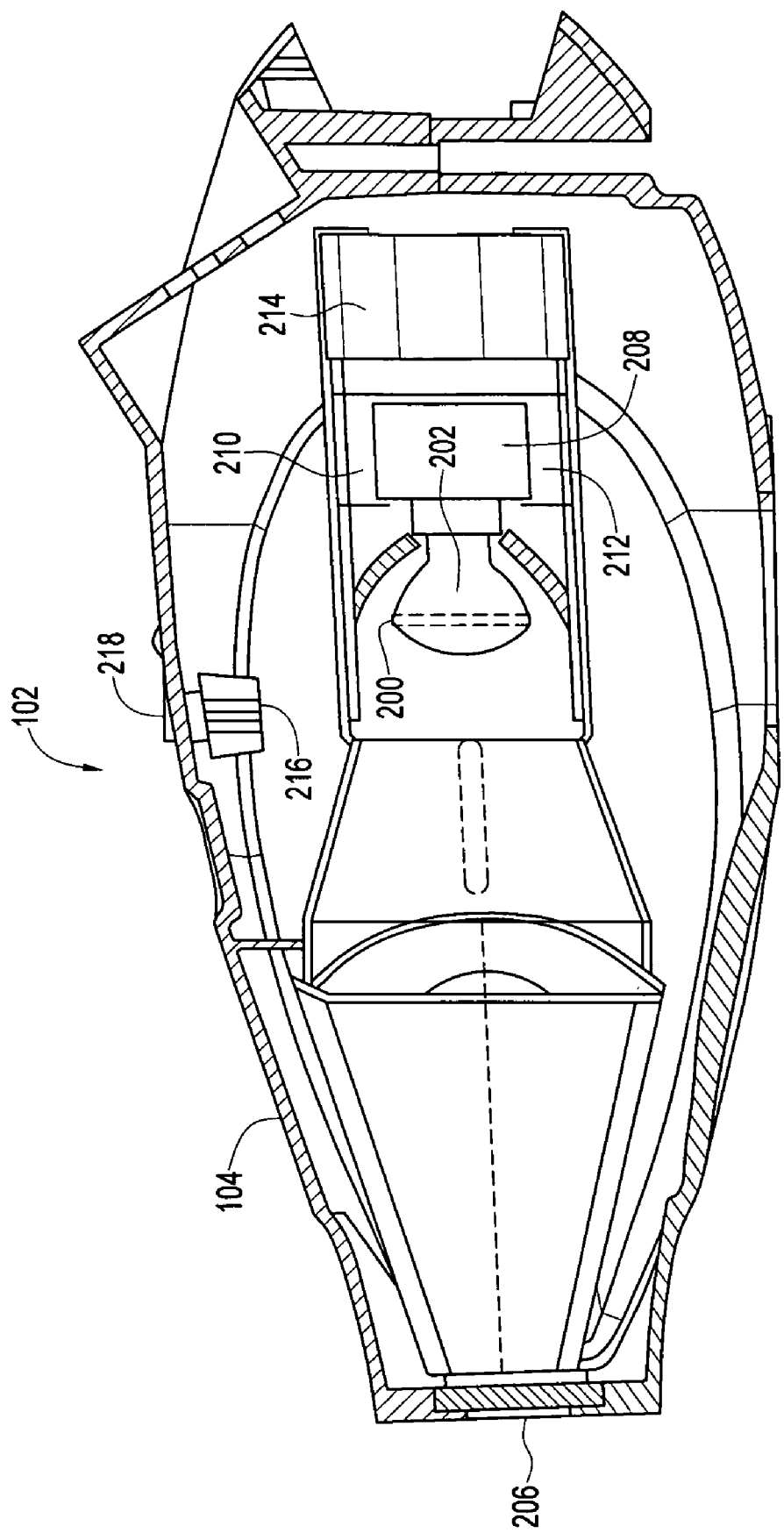
FIG. 2 shows, in cross section, various components of a whitening or curing lamp head, according to one embodiment of the invention.

FIG. 2 shows, in cross section, various components of the lamp head 102 according to one embodiment of the invention. As discussed above, the lamp head 102 includes a housing 104. A light source 200 is disposed within the housing 104. In the pictured embodiment, the light source 200 includes a first reflector 202 integral to the light source 200. The housing 104 includes an aperture 206 adapted to allow passage of light from the light source out of the housing 104.

According to the illustrated embodiment, the light source 200 includes an arc lamp such as a halogen light source. In various alternative embodiments, the light source 200 may include a lamp, semiconductor light emitting devices, light-emitting chips such as an LED, a solid state LED, an LED array, a fluorescent bulb, an incandescent lamp, a solid-state laser, a gas laser, or similar, alone or in combination. The light source is identified here are merely exemplary, and one of skill of the art will appreciate that the invention in its various aspects may include any of a wide variety of current or future light sources.

In the illustrated embodiment, the light source 200 is coupled to an electrical ballast 208. According to one embodiment, the ballast 208 is disposed in proximity to a heat sink 210. Pursuant to one embodiment of the invention, the heat sink 210 includes a plurality of radial vanes 212. In another embodiment, the heat sink can be made of any material that has good thermal conductivity, including metal blocks of copper, aluminum or similar materials. In another embodiment, the cooling system includes heat pipes. In another embodiment, the cooling system includes phase change materials. Some embodiments and materials are exemplified in U.S. Application No. 60/585,224, "Dental Light Devices With Phase Change Material Filled Heat Sink", filed on Jul. 2, 2004, the contents of which are incorporated herein by reference. Also according to the illustrated embodiment, a cooling fan, such as electric boxer fan 214 is disposed within the housing 104.

Heat sinks having a phase change material may more efficiently remove or divert heat from a light source or sources with a given weight of heat sink material when compared to a heat sink made of a solid block of thermally conductive material such as metal. Such a heat sink may even efficiently remove or divert heat from a curing light device when a reduced weight of the material is used. Using a phase change material enclosed inside a hollow thermally conductive material such as a metal heat sink instead of a conventional solid metal heat sink can decrease the weight of the curing light and increase the time the heat sink takes to reach the "shut off" temperature, as it is called in the dental curing light industry.

The period prior to reaching the shut off temperature is called the "run time". Increasing the "run time", i.e., the time that the light can remain on, increases the time when a dentist can perform the curing or whitening procedure.

In one embodiment, a rechargeable dental curing light including at least one phase change material is disclosed. In another embodiment, a dental whitening light including at least one phase change material is disclosed. The heat sink includes a block of thermally conductive material, such as metal, having a bore or void space which is at least partially filled with a phase change material.

The heat sink may be constructed by hollowing out a thermally conductive material, such as metal, and at least partially filling the void with at least one phase change material prior to capping it to secure the phase change material inside, such that the at least one phase change material is substantially contained or surrounded by a thermally conductive material such as metal normally used in the construction of a conventional heat sink.

Alternatively, the heat sink may be cast or machined from a thermally conductive material, such as metal, to create walls surrounding a bore or void. The bore or void is partially filled with at least one phase change material prior to capping it to secure the material inside.

In one embodiment, the inventive heat sink may be used by itself. In another embodiment, it may be used in addition to a fan, in conjunction with a conventional metal block heat sink or combinations thereof.

The inventive heat sink may be installed into the dental curing light, imaging or whitening light source in the same manner a conventional metal block heat sink is installed, such as by attaching it to the heat generating source, i.e., the light source, which may include any of the ones mentioned above or combinations thereof, or by attaching it to another heat sink.

Suitable phase change material may include organic materials, inorganic materials and combinations thereof. These materials can undergo substantially reversible phase changes, and can typically go through a large, if not an infinite number of cycles without losing their effectiveness. Organic phase change materials include paraffin waxes, 2,2-dimethyl-n-docosane ($C_{24}H_{50}$), trimyristin, (($C_{13}H_{27}COO)_3C_3H_3$), and 1,3-methyl pentacosane ($C_{26}H_{54}$). Inorganic materials such as hydrated salts including sodium hydrogen phosphate dodecahydrate ($Na_2HPO_4.12\ H_2O$), sodium sulfate decahydrate ($Na_2SO_4.10H_2O$), ferric chloride hexahydrate ($FeCl_3.6H_2O$), and TH29 (a hydrated salt having a melting temperature of 29° C., available from TEAP Energy of Wangara, Australia) or metallic alloys, such as Ostalloy 117 or UM47 (available from Umicore Electro-Optic Materials) are also contemplated. Exemplary materials are solids at ambient temperature, having melting points between about 30° C. and about 50° C., more for example, between about 35° C. and about 45° C. Also, the exemplary materials have a high specific heat, for example, at least about 1.7, more for example, at least about 1.9, when they are in the state at ambient temperature. In addition, the phase change materials may, for example, have a specific heat of at least about 1.5, more for example, at least about 1.6, when they are in the state at the elevated temperatures.

The phase change material may also have a high latent heat of fusion for storing significant amounts of heat energy. This latent heat of fusion may be, for example, at least about 30 kJ/kg, more for example, at least about 200 kJ/kg.

Thermal conductivity of the materials is a factor in determining the rate of heat transfer from the thermally conductive casing to the phase change material and vice versa. The thermal conductivity of the phase material may be, for example, at least about 0.5 W/m° C. in the state at ambient temperature and at least about 0.45 W/m° C. in the state at elevated temperature.

In general, the phase change material may be contained inside a thermally conductive material, such as a metal casing. The casing defines a bore, which may be of any shape, but is for example, generally of a cylindrical or rectangular shape. The metal casing or wall of the bore acts to contain the phase change material, and to also aid in conducting heat to and away from the phase change material. The thinner the wall, the more phase change material can be present in a given size of the heat sink, and the less it contributes to the weight of, for example, the curing light. However, the thinner the wall, the less efficient the heat sink maybe in conducting heat away from the phase change material and the longer it will take to return the phase change material to ambient temperature and its original state, so that it may function as a heat sink again. For example, the wall thickness ranges from about 1 mm to about 2.5 mm, more for example, from about 1 mm to about 1.5 mm.

The casing may also be constructed to have a large surface area. A structure having fins or other features that serve to increase the surface area for heat conduction or convection is desirable, thus a spherical structure, though useful, is not the optimal choice. Such fins or other surface area increasing features may also be incorporated into the bore to increase the contact area between the thermally conductive casing and the phase change material, thus permitting faster more efficient transfer of heat between the thermally conductive casing and the phase change material.

The thermally conductive casing can also provide a good thermal contact for heat transfer from the light source. This may be accomplished with a smooth, thermally conductive surface with a high area of contact. Also, thermal coupling may be achieved with thermally conductive interface materials such as thermal epoxy. Interface materials that are electrically insulating are also useful in isolating the light source from the heat sink in an electrical sense without losing thermal conductivity.

One embodiment of the invention includes an indicator module 216 coupled to an internal surface on the housing 104. In the illustrated embodiment, the indicator module 216 includes a plurality of light emitting diodes 218. According to one embodiment of the invention, the light emitting diodes 218 are adapted to provide an indication of an operational status of the dental lamp to a user. In another embodiment of the invention, the indicator module 216 includes a lamp head memory device 324 (shown in FIG. 3), such as a memory integrated circuit device. The lamp head memory device may be any one of wide variety of memory devices, such as are known in the art. For example, the lamp head memory device 324 may be an electrically programmable read only memory integrated circuit device (EPROM), an erasable electrically programmable read only memory integrated circuit device (EEPROM), a flash memory integrated circuit device, a resistant memory device such as a magnetoresistive integrated circuit memory device (MRAM), or a programmable metallization resistive memory device (PRAM), an optical memory device, or any other appropriate recording medium adaptable to serve as a memory device for storing information.

Figure 3:
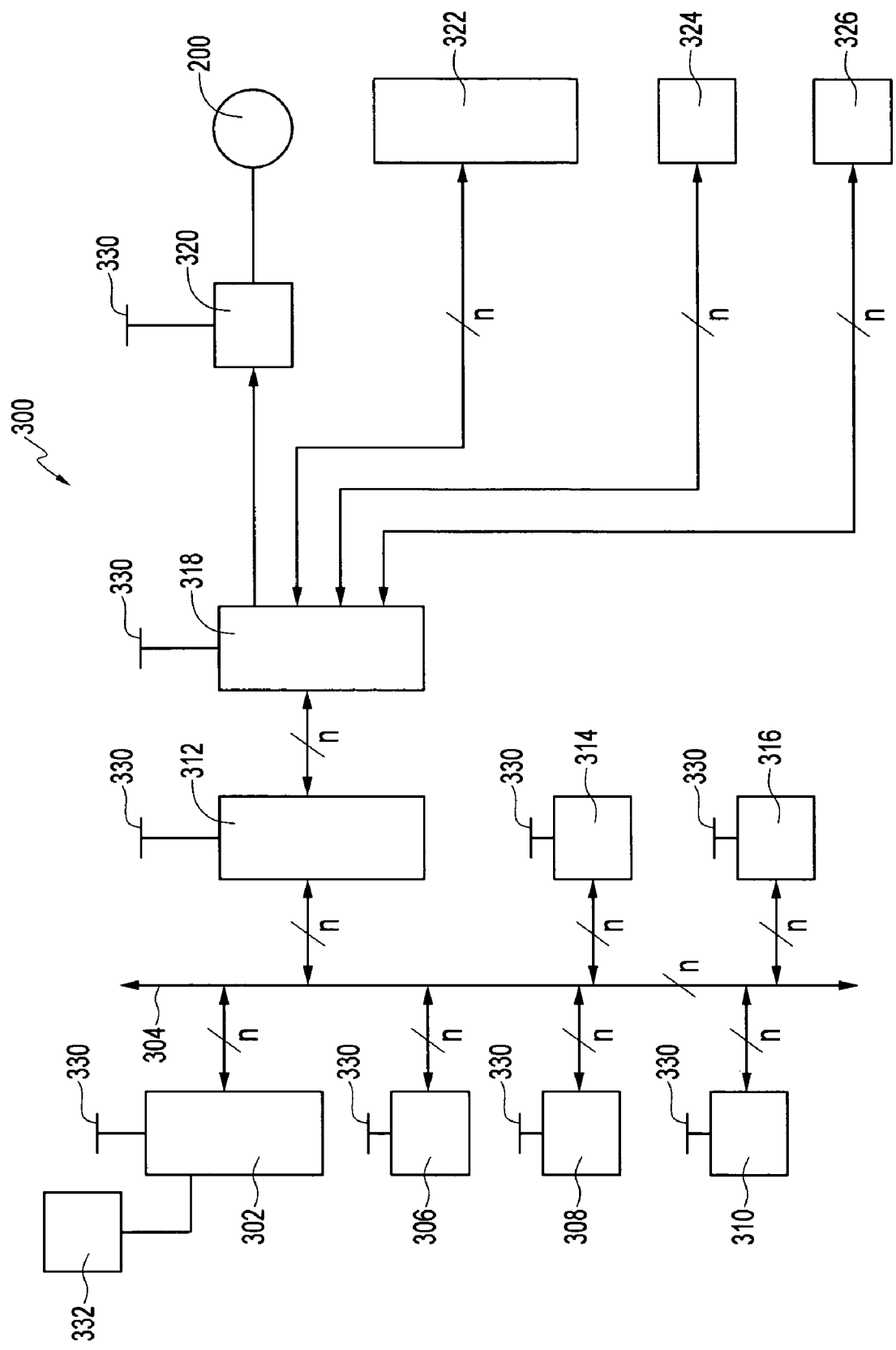
FIG. 3 shows, in block diagram form, a control system according to one embodiment of the invention.

FIG. 3 shows, in block diagram form, various aspects of a dental lamp controller 300 according to one embodiment of the invention. In the illustrated embodiment, the dental lamp controller 300 includes a central processing unit 302, such as, for example, an integrated circuit microprocessor device. The central processing unit 302 may be coupled to a communication bus 304. According to one embodiment of the invention, the communication bus 304 is a parallel bus including data and control signal lines. According to another embodiment of the invention, the communication bus 304 is a serial communication bus. According to still another embodiments of the invention, the communication bus 304 combines, in various aspects, serial and parallel structural features.

Also coupled to the communication bus 304, in the illustrated embodiment, is a program storage memory device 306. In another aspect of the presently-disclosed embodiment the communication bus 304 may be coupled to a data storage device 308. According to one embodiment of the invention, the program storage memory device 306 and the data storage memory device 308 are discrete devices, such as, for example, solid-state memory devices.

In another embodiment of the invention, the program storage memory device 306 and data storage memory device 308 are implanted as a single integrated circuit memory device. According to one embodiment of the invention, memory devices 306 and 308 are dynamic random access memory (DRAM) devices. In another embodiment of the invention, memory devices 306 and 308 are static memory devices. In still other embodiments of the invention, as would be understood by one of skill of the art, memory devices 306 and 308 may be implemented as flash memory, magneto-resistive random access memory (MRAM), programmable metallization memory (PRAM), or other memory devices, such as are known or may be developed.

According to a further embodiment of the invention, a read-only memory device 310 such as a ROM, PROM, EPROM, or EEPROM, is coupled to the communication bus 304. In addition, an I/O port device 312 may also be coupled to the communication bus 304. According to still other embodiments of the invention, the communication bus 304 may be coupled to a communication device such as, for example, a universal receiver asynchronous transmitter (UART) 314, and to a further memory storage device 316 such as, for example, a floppy disk drive, a hard disk drive, an optical disk drive, a removable flash memory device, or another memory device as noted in the art.

In the illustrated embodiment, the communication bus 304 is shown as having a uniform signal width n. In various embodiments of the invention, however, the entire bus or a portion thereof may be coupled to various devices.

According to the illustrated embodiment, the controller 300 includes a driver device 318 having an input signally coupled to an output of the output port 312. As illustrated, in various embodiments of the invention, the driver device 318 may be coupled at respective outputs thereof to corresponding inputs of a switching device 320, a user interface device 322, a lamp head memory device 324 and a light guide memory device 326.

The control system embodiment of 300 shown in FIG. 3 also includes a light source 200 coupled to switching device 320. The switching device 320 may be adapted to control the illumination of the light source 200 based on a signal received at an input of the switching device 320 from a respective output of the driver device 318. Accordingly, the switching device 320 may also be coupled to a source of lamp power such as a first voltage supply 328.

In various embodiment of the invention, the switching device 320 may be a transistor switching device, a silicon controlled rectifier device, a thyristor device, an optically isolated switching device, an electromechanical relay, or any one of the number of control devices known to one of skill in the art.

According to one embodiment of the invention, various other devices of the control system (302, 306, 308, 310, 312, 314, 316, 318, etc.) are each respectively coupled to a source of logic power, such as a second voltage supply 330. As would be understood by one of skill in the art, the first voltage supply 328 and second voltage supply 330 may, according to various embodiments, consist of a single voltage supply device supplying a signal voltage, or may include two or more voltage supply devices providing a plurality of different voltages.

In still another aspect of the invention, according to one embodiment, the central processing unit 302 is coupled to a clock signal source 332. As would be understood by one of skill of the art, the clock signal source 332, or other clock signal sources, may also be coupled to one or more other devices of the control system 300.

In a typical operation, the control system 300 would transfer a plurality of program commands from a substantially permanent memory storage device such as read only memory 310 or memory storage device 316 into a transient memory storage device such as program storage memory device 306. As would be understood by one of skill in the art, this transfer may be effected by sequentially transferring each program command of the plurality of program commands from the substantially permanent memory storage device 310, 316 into the central processing unit 302 and thereafter into the transient memory storage device 306. Alternately, the transfer may be effected by a direct memory access (DMA) transfer.

Thereafter, the central processing unit reads the plurality of program commands out of the transient memory storage device 306 and into the central processing unit 302 according to a program structure encoded in the plurality of program commands, and according to various external inputs received by the central processing unit 302 (as, for example, from the I/O device 312).

During execution of the program steps by the central processing unit 302, data values produced by the central processing unit 302 are stored in the data memory device 308. Also, the central processing unit 302 retrieves the stored data values from the data memory device 308 according to the sequence of program steps executed. In addition, according to various embodiments of the invention, data values are stored in the permanent data storage device 316, or are communicated to an external device by way of the UART 314.

As will be discussed in further detail below, the central processing unit 302 also communicates with the switching device 320, the user interface device 322, the lamp head memory device 324, and the light guide memory device 326, to receive data from these devices and to affect respective internal states thereof. In particular, according to one embodiment of the invention, the central processing unit 302 receives control data from the user interface device 322 and based on that control data, reads a state of light guide memory device 326. Responsive to the state of light guide memory device 326, the central processing unit 302 executes a program decision resulting in a binary signal received at switching device 320. Depending on a state of the binary signal received at switching device 320, light source 200 is either illuminated, or not illuminated during a particular time interval.

In one embodiment of the invention, a power supply device is provided that supplies system power at about 12 volts. In another embodiment, the power supply device supplies system power at a voltage of about 5 volts.

Figure 4:
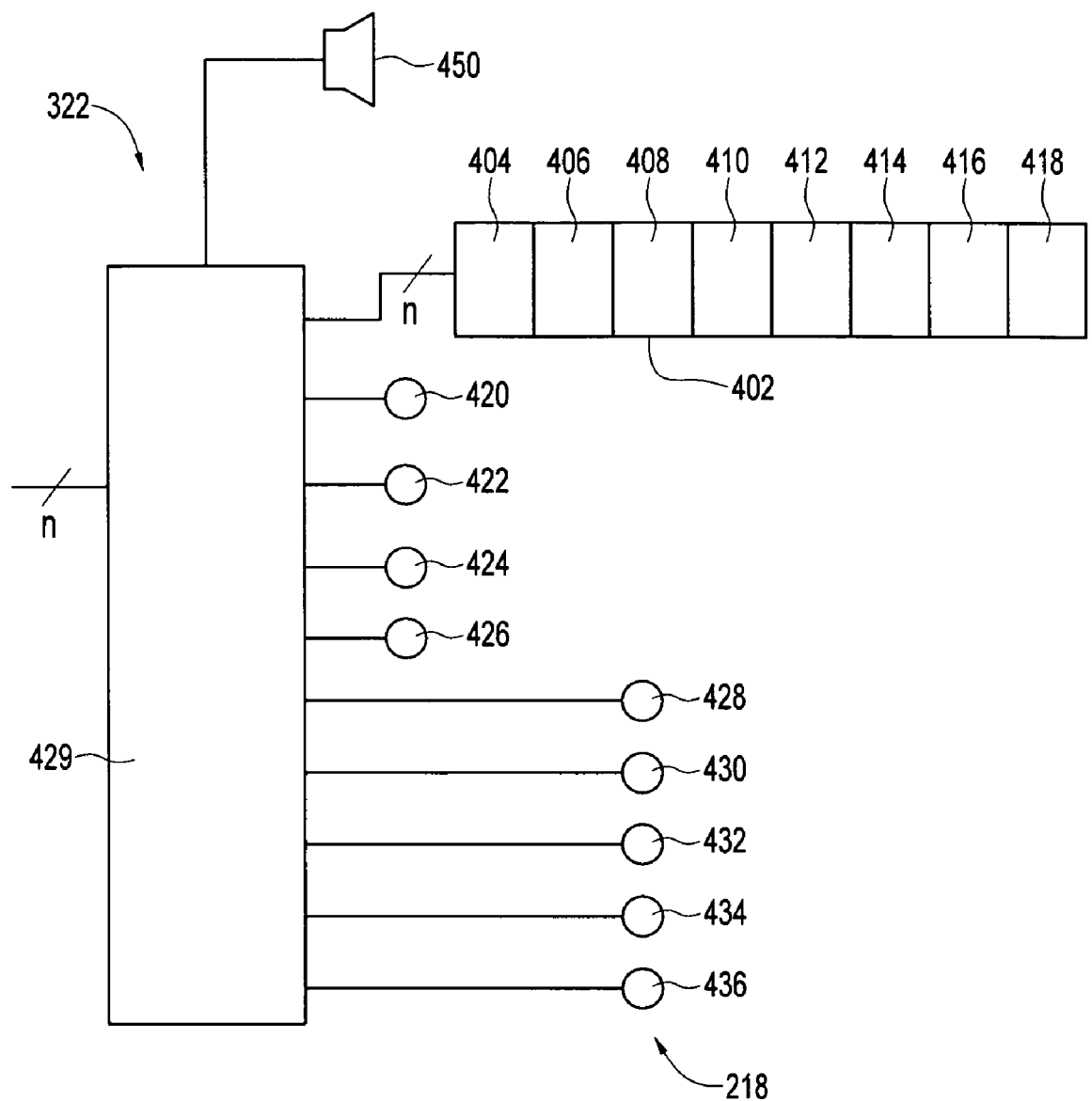
FIG. 4 shows, in block diagram form, aspects of a control system according to one embodiment of the invention.

FIG. 4 shows a user interface device 322, such as that of, for example, the control system 300 (shown in FIG. 3). The user interface device 322 includes a liquid crystal display (LCD) module 402 having the ability to display for example, eight alphanumeric characters (404, 406, 408, 410, 412, 414, 416, 418). The user interface device 322 also includes four push button switches. According to one embodiment of the invention, the switches are designated "ON" 420, "OFF" 422, "START" 424 and "PAUSE" 426. According to one embodiment of the invention, the user interface device 322 also includes a multiplexing device 429. The multiplexing device 429 is adapted to couple various elements of the user interface device to the driver device 318 (as shown in FIG. 3).

Also shown in FIG. 4 is a plurality of light emitting diodes 218 that serve to indicate an operational status of the lamp to a user. According to one embodiment of the invention the light emitting diodes 218 include an indicator 428 that is adapted to be illuminated by the control system when light source 200 has achieved and exceeded its design lifetime.

According to a further aspect of the disclosed embodiment, indicators 430, 432, 434 and 436 are provided to indicate a past and remaining proportion of an operational interval of the light system. For example, if a whitening lamp system 100 is being used to illuminate a dental compound during a particular interval, indicator 430 is illuminated immediately upon commencement of the processing interval and remains illuminated throughout the processing interval. Indicator 432 is illuminated after one quarter of the processing interval has elapsed. Thereafter indicator 432 remains illuminated for the balance of the processing interval. Indicator 434 is illuminated after one half of the processing interval has elapsed. Thereafter indicator 434 remains illuminated for the amount of the processing interval and indicator 436 is illuminated after three quarters of the processing interval has elapsed and remains illuminated for the balance of the processing interval.

One of skill in the art will appreciate that indicators 420, 422, 424, 426, 428, 430, 432, 434 and 436, while described here as light emitting diodes, may be any of a wide variety of indicators such as are known in the art. For example the indicators may include incandescent light bulbs, gaseous discharge lamps including fluorescent light bulbs, neon (or other noble gas) light bulbs, and other plasma display devices, laser devices, and other light generating devices such as are known in the art as well as audible enunciators and other indicators appropriate to notify the user such as a dental professional of system status.

According to one embodiment of the invention, drivers are provided to sink current from the indicators. In one embodiment of, the drivers are capable of sinking a current of approximately 2 mA per indicator, and in another embodiment, the drivers are not current limited.

In a further embodiment of the invention, the control system includes a lamp driver that is capable of sinking a current of approximately 1.5 A to drive the light source 200.

FIG. 4 also shows a speaker, or other acoustic transducer 450, adapted to produce an audible beep or tone, or other audible indication of system status. According to one embodiment of the invention, the audible indication of system status includes a synthesized or recorded voice simulation. In another aspect of the invention, the audible beep or tone includes a beep having a frequency of the for example, about 2 kHz and a duration of, for example, approximately one-half second or longer. In another allotment of the invention, the audible beep or tone includes a beep having a frequency of, for example, about 200 Hz and a duration of, for example, about one-half second or longer. In another embodiment of the invention, the audible beep or tone includes a beep having a frequency of, for example, about 1 kHz and a duration of, for example, about one-half second or longer. According to one embodiment of the invention, this 1 kHz tone is used to indicate the completion of a timing function or the near completion of a timing function.

In a further embodiment, a control system having a built-in voice alert system for alerting a dental professional of the time, or stage, in a dental procedure may be included. The control system may also include a headphone or other private listening device, for example, so that only the dental professional will receive the voice alert. In one aspect, the private listening device may be a wireless listening device such as a wireless radio channeling device or an infrared channeling device.

In one embodiment, the control system includes a built-in electronic voice alerting system to alert the dental professional of the completion of a dental procedure.

In one aspect, the electronic voice alerting system may utilize an electronic voice generating circuit technology, similar to the technology used in electronic devices such as toys, cell phones, automobiles and other consumer electronics, but with novel message content that is directed to dental applications.

In still another embodiment, a control system includes an audible electronic voice alert system having a novel approach to tracking time during the above mentioned dental procedures and other similar dental procedures. This audible electronic voice alert system uses an electronic device with pre-recorded time interval statements stored in the device.

According to one embodiment, the alert system, in addition to having the lighted indicators mentioned above, is also adapted to play a recorded voice that is generated when an electronic timer circuit is programmed to play the appropriate electronic voice count alert through an audio speaker in the device. In one aspect, the message played may include time intervals, and may be programmed and in some embodiments, re-programmed.

In a further embodiment, a control system having an electronic timer device is controlled by a microprocessor with an internal clock. The microprocessor receives a signal so as to know when a lamp is first turned on. At predefined intervals of, for example, five seconds, the electronic voice chip sends a recorded audio signal to a speaker to announce elapsed and/or remaining time to the user. In one embodiment of the invention, the speaker is disposed within the light source. This process may be programmed to continue and announce the ten second intervals when the voice chip releases a different recorded audio signal of "ten seconds". Various time increments and corresponding audio signals can be programmed or selected according to the requirements of a particular dental procedure.

In yet a further embodiment of the invention, a control system includes a prerecorded audio stream that may be configured to play a unique alert message at the end of a procedure. The pre-recorded audio signal can include a message such as "procedure complete", "end of a first cycle" when used in chairside whitening procedures, or similar phrase. Additionally, the system may be configured to give instruction to the dental professional at certain times during the procedure. Exemplary messages may include prerecorded audio streams announcing, "the procedure is almost complete", "please plan for the next step in the whitening process", and "whitening lamp warm up cycle complete." Numerous and various such voice alerts are possible and are intended to be within the scope of this invention.

In a yet still further embodiment, the invention, includes a voice alert system coupled to an electrical control device. The electrical control device may include a microprocessor and a switch such as an electromechanical switch or a solid state switch. In various embodiments, the electrical control device may be adapted to both alert the dental professional of the end of the procedure, and to also turn off the light output, when the predetermined time period has expired. This may further improve the efficiency and accuracy of a dental procedure and free the dental professional to take care of other matters within earshot of the voice alert system rather than having to hover around the patient or be close at hand to turn off the lamp. In one aspect, the alert system may be equipped with a patient to dentist and/or dental practitioner call device.

Figure 5:
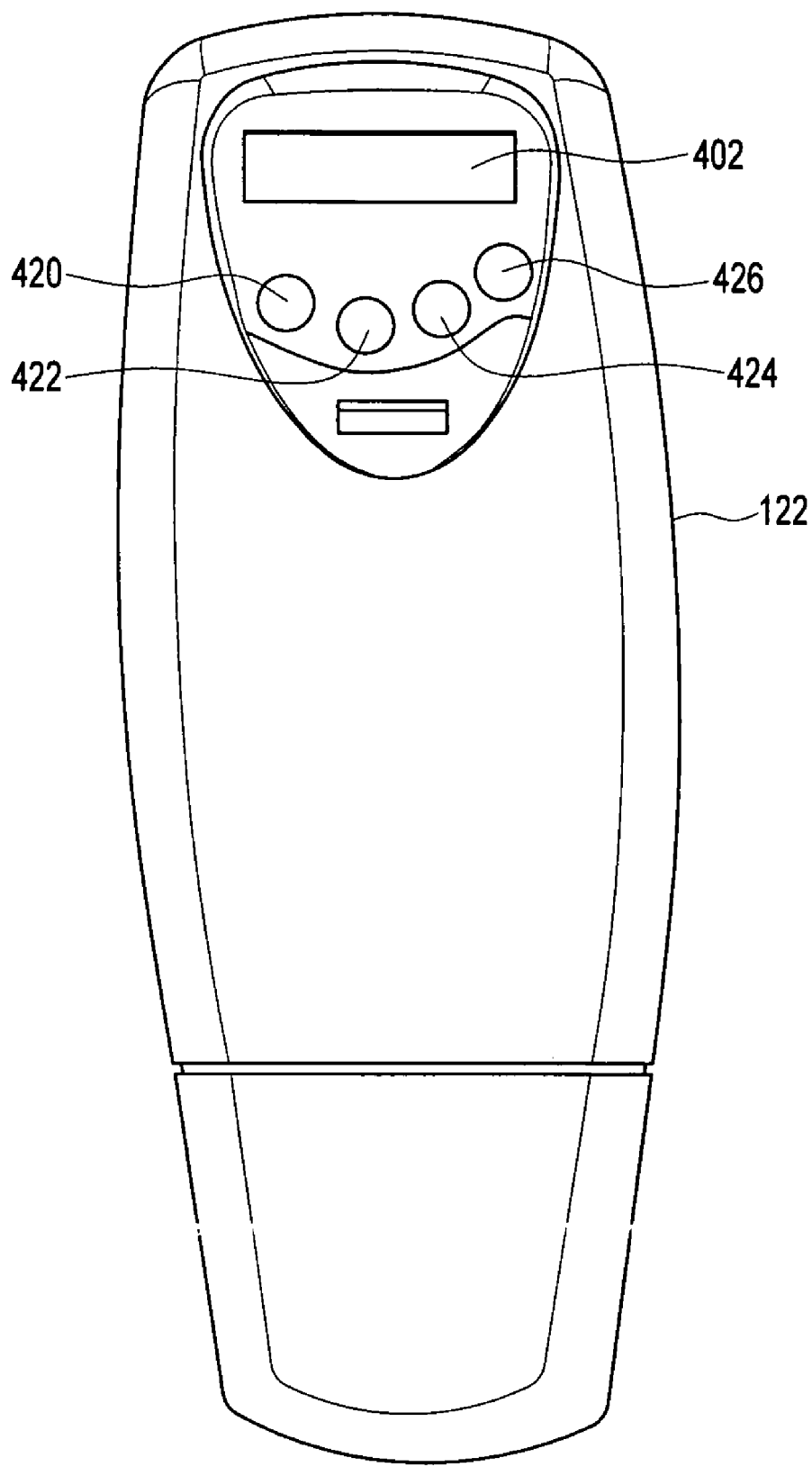
FIG. 5 shows a power pack including a user interface according to one embodiment of the invention.

FIG. 5 shows an exemplary arrangement of the user interface device according to one embodiment of the invention. As shown, the user interface device is disposed on the power pack module 122. FIG. 5 illustrates the LCD module 402, and four pushbutton switches 420, 422, 424 and 426.

As noted above, it is desirable to control usage of a disposable light guide so that its use can be limited to a single dental patient. This can allow the light guide to be prepared as a non-reusable consumable) item having various hygienic and economic benefits associated therewith. Generally, it may be desirable to control the replacement of various dental lamp components including, for example, the light guide, and the light source, such as the light bulb. With this in mind, according to one embodiment of the invention, the lamp head includes a first memory device 324 (as shown in FIG. 3) and the light guide includes a second memory device 326 (also as shown in FIG. 3).

During operation of the dental lamp, the dental lamp control system reads and evaluates first and second data sets of data stored within the first memory device 324 and second memory device 326 respectively. According to one embodiment of the invention, a null data set indicates that a subsystem associated with the memory device is unused. Accordingly, a null data set in the first memory device 324 related to the light source 200, (as shown in FIG. 2) indicates that the light source 200 is unused, and is anticipated to be available, for example, about for 100 hours of use. In like fashion, a null data set in the second memory device 326 indicates that the light guide 120 (as shown in FIG. 1) is unused, and may be used on a new patient.

During operation of the lamp (i.e., while the light source 200 is illuminated) the central processing unit 302 (as shown in FIG. 3) causes data to be written to both the first memory device 324 and the second memory device 326. Consequently, the first memory device 324 and the second memory device 326 thereafter each exhibits a non-null data set stored respectively therewithin. As a result, during subsequent read cycles of the control system, the non-null data set indicates the above-described usage of the light guide 120 and illumination source 200.

Figure 6:
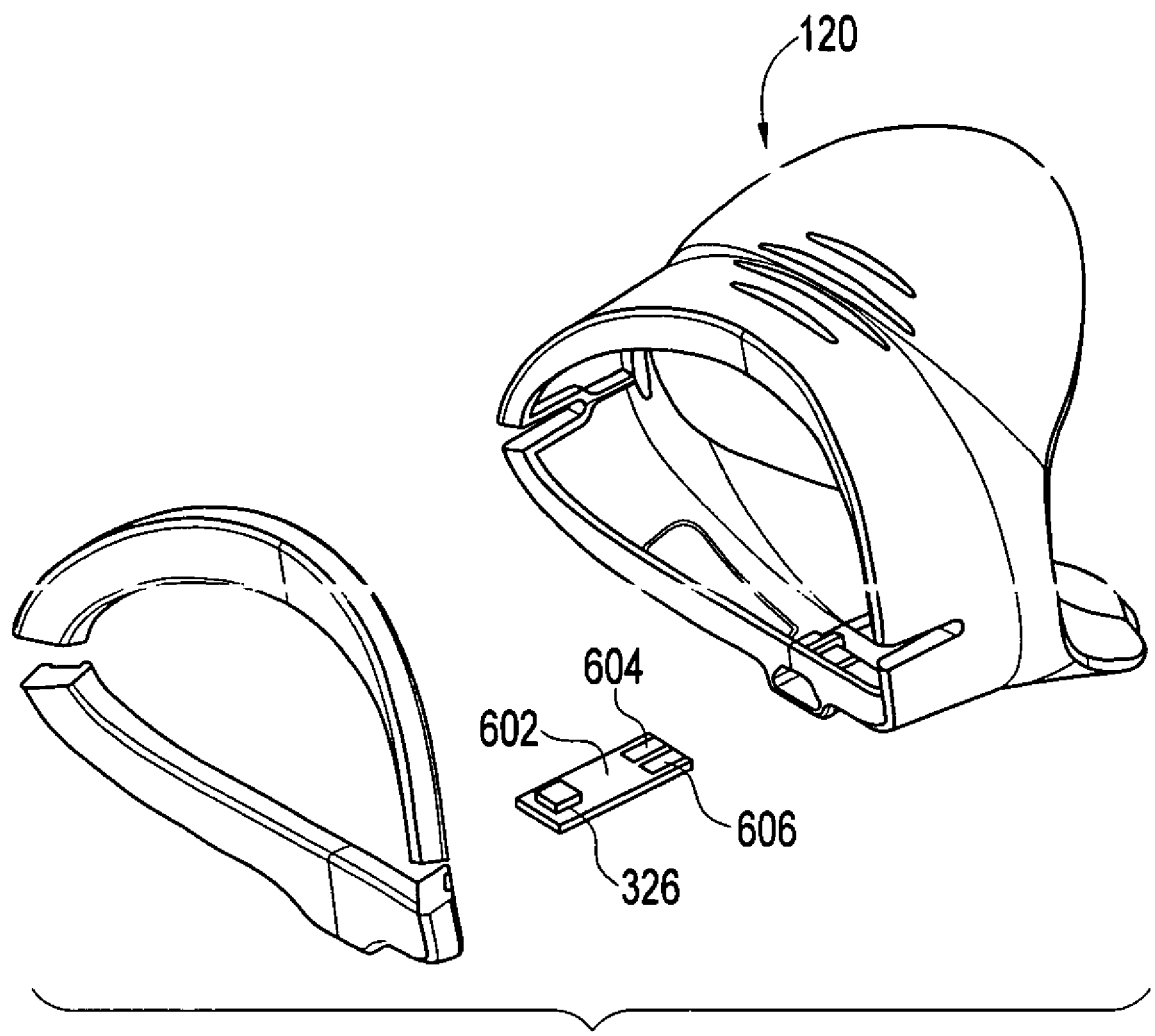
FIG. 6 shows a light guide including a memory integrated circuit device according to one embodiment of the invention.

FIG. 6 shows, in exploded view, a light guide 120 according to one embodiment of the invention. The light guide 120 includes a memory device 326. In the illustrated embodiment, the memory device 326 is mounted on a printed wiring board 602. Also in the illustrated embodiment, the printed wiring board 602 includes first and second electro-mechanical contacts 604, 606. These electromechanical contacts 604, 606 are adapted to engage a corresponding socket within the lamp head housing 104 when the light guide 120 is mechanically coupled to the lamp head housing 104. As a result, contact 604, 606 served to removably electrically couple the memory device 326 to the central processing unit 302 (as shown in FIG. 3).

Figure 7:
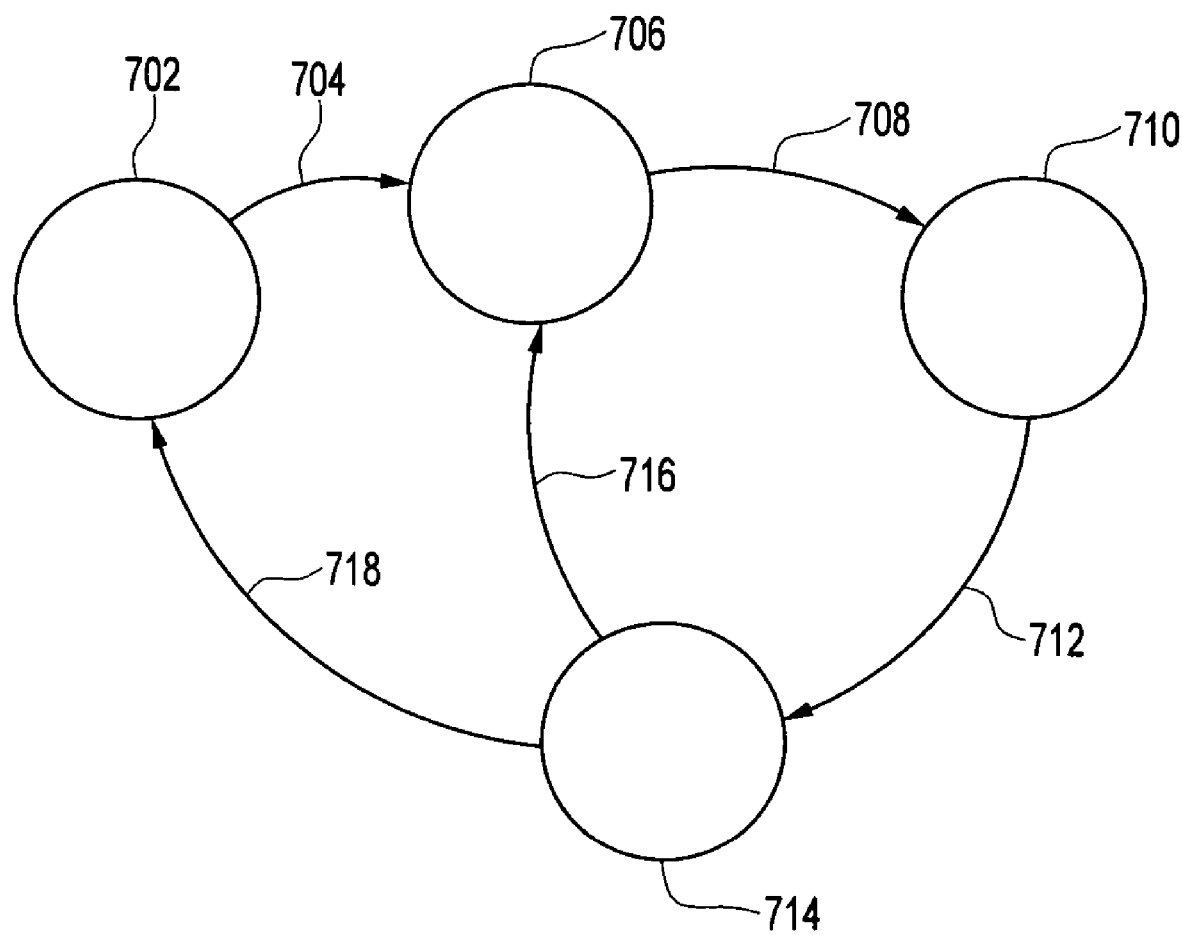
FIG. 7 shows a state diagram representing operation of a control system according to one embodiment of the invention.

FIG. 7 shows a high-level state diagram 700 illustrating various aspects of an operation of a lamp control system such as, for example, that of FIG. 3, according to one embodiment of the invention. The state diagram 700 reflects usage control of a light guide 120 (as shown for example in FIG. 1). The state diagram 700 illustrates a control method adapted to provide illumination for activation of a dental whitening compound. One of skill in the art will appreciate that a wide variety of control methods may be effected by the preparation of an appropriate plurality of program commands such as is made clear by the exemplary embodiment of FIG. 3.

The state diagram 700 shows an initial state 702 of the dental lamp control system. In initial state 702, an unused light source 200 (as shown in FIG. 2) is present in the lamp head 102. To activate the light source 200, an unexpended light guide 120 is coupled to the lamp head 102. The central processing unit, under program control, reads and evaluates 704 a data set as stored in a light guide memory device 326. If the data set in the light guide memory device 326 indicates that the light guide is unexpended, then the control system enters a ready state 706. A user input 708, as for example, depressing a pushbutton switch, causes the system to transition into a run state 710.

In the run state 710 the light source 200 is activated under the control of the central processing unit 302 by means of a signal set from the center processing unit 302 to the switching device to 320 (as shown in FIG. 3). State diagram 700 is simplified to indicate that the system remains in a run state until either a further user input ("stop" signal) is received, or until a time interval of a particular duration has elapsed. This simplified operation corresponds to one embodiment of the invention. In another embodiment of the invention, various other states may be entered. For example, the time interval may be broken up into a plurality of shorter time intervals of, for example, 15 minutes each. According to such embodiment, the light source would be turned off by the control system after every 15 minute time interval, and for such time intervals would be included within the run state 710.

State diagram 700 includes a state transition 712 out of the run state 710 upon receipt of a user input or after the time interval has elapsed. Thereafter, the control system enters a lamp used state 714 corresponding to a non null data set disposed within the lamp head memory device 324. At the same time the data set of the light guide is "full", indicating that the light guide has been expended and that no further use of the light guide may be made. Consequently, if upon reading the light guide memory device 326 the central processing unit 302 detects this "full" data set, the control system will remain in the state 714 until an unexpended light guide is coupled to the lamp head 716, or until the light source 200 is replaced and the data set within the lamp head memory device 324 is cleared or reset to null, resulting in state transition 718.

Figure 8:
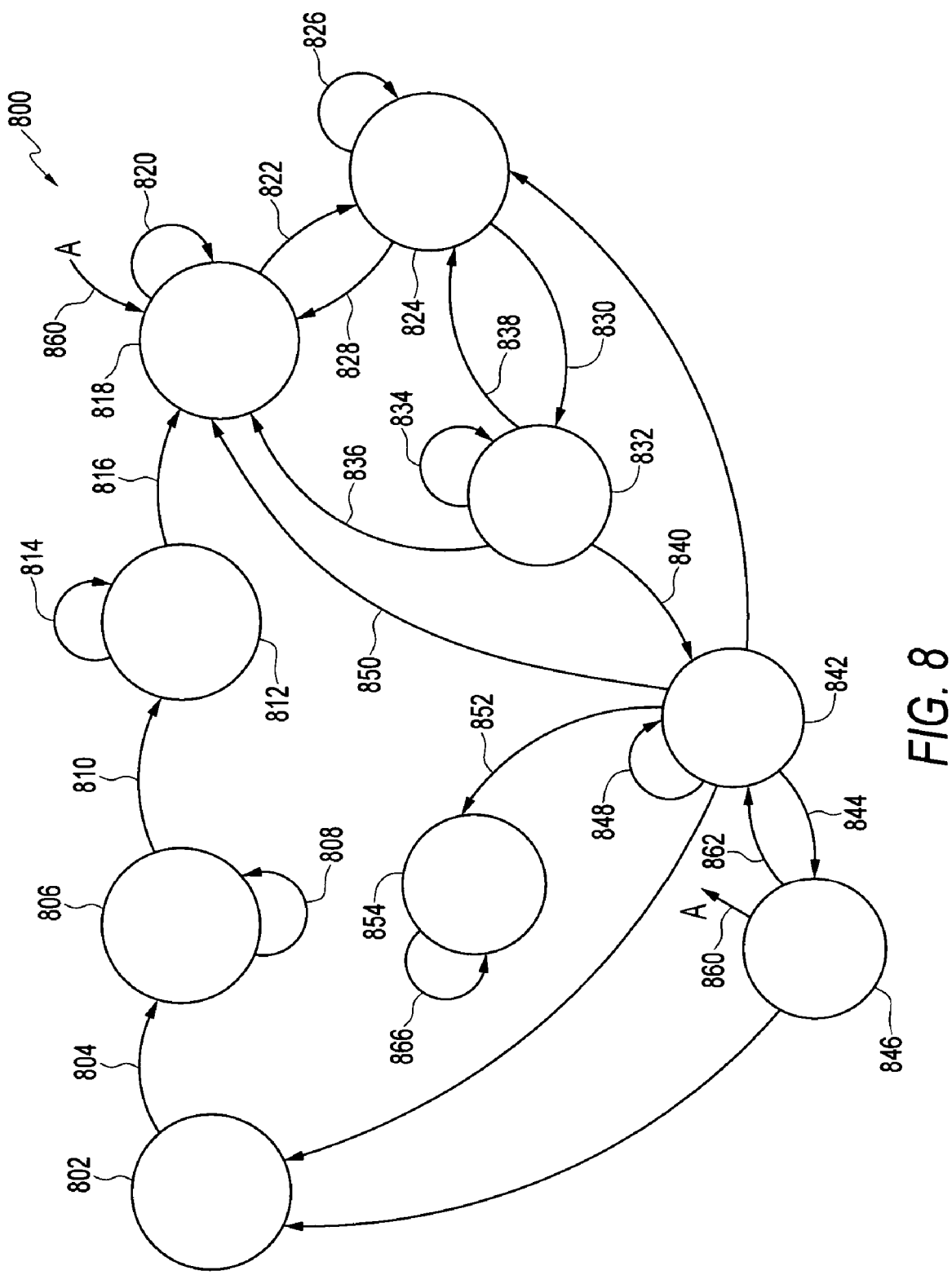
FIG. 8 shows a state diagram represent the operation of a control system according to one embodiment of the invention.

FIG. 8 shows a state diagram 800 representing operation of a control system according to one embodiment of the invention. As shown in FIG. 8, during a first time interval, the control system occupies a first "off" state 802.

A first state transition 804 is effected when the control system is powered up with no push buttons being held down, and with no manufacturing jumper installed. Execution of state transition 804 results in the control system entering a "power-up" state 806.

In power-up state 806 light source 200 (as shown in FIG. 2) is off as are indicator LEDs 218 (as shown in FIG. 4). According to the present embodiment of the invention, the liquid crystal display device 402, for example, (also as shown in FIG. 4) displays a preselected communication or value such as "ZOOM2." A lamp restart timer is activated 808. According to one embodiment of the invention, the lamp restart timer is set to timeout after an interval of 10 seconds.

Upon completion of the timeout interval, the system makes a state transition 810 to a version display state 812. According to one embodiment of the invention, while the system is in version display state 812 the liquid crystal display device displays "VER x.x," where x.x is replaced by the current version number of the system firmware. This display is active for a brief duration 814 (for example 10 seconds) after which the system again makes a state transition 816 to a "KEY" state 818.

While the system is in key state 818 the messages "ATTACH" and "GUIDE" are alternately and repetitively displayed on the liquid crystal display device 402. While in this state 818, the light source device 200 remains in the off (or non-illuminated) state. Also, while the system is in the KEY state 818, the input port for receiving data from the light guide memory device 326 is repetitively polled 820 to see whether a light guide 120 is attached to the system. During this state 818, none of the input buttons 420, 422, 424, 426 are active. That is to say, depressing any of the buttons, alone or in combination, does not produce a change of state of the system.

The system remains in KEY state 818 until polling of the light guide memory device port indicates that a light guide 120 has been coupled to the system. Thereafter, the system makes a transition 822 to an "OFF" state 824.

While the system is in the OFF state 824, the text "READY" is continuously shown on the user interface display 402. The ON button 420 is active and able to receive input into the system. Also, the input port for receiving data from the light guide memory device 326 is repetitively polled 826 to see whether the light guide 120 remains attached to the system. If the light guide is found not to be present, i.e., the key input is found to be in a stable inactive state, the system transitions 828 back to the key state 818.

Depressing the ON button 420 causes a state transition 830 to "READY" state 832. In the READY state 832, the light source 200 remains inactive (off). The light emitting diodes, or other status indicators 218 (as shown in FIG. 4) also remain in active (off). The LCD display 402, (also as shown in FIG. 4) displays alternately and repeatedly the text "PRESS" and "START."

Various state transitions are available out of the READY state 832. For example, while the system is in the READY state, the input port for receiving data from the light guide memory device 326 is repetitively polled 834 to see whether the light guide 120 remains attached to the system. If the light guide is found not to be present, i.e., the key input is found to be in a stable inactive state, the system transitions 836 back to the KEY state 818.

Activation of the OFF input 422 (as for example by finger pressure applied to the input button) causes a transition 838 from the READY state 832 to the OFF state 824.

Similarly, pressing the "START" button 424 causes a transition 840 from the READY state 832 to the RUN state 842. It should be noted that pressing the ON button 420 while in the READY state 832, has no effect and causes no state transition. Likewise, pressing the PAUSE button 426 while in the READY state 832 has no effect and causes no state transition.

In addition, it should be noted that the system may be configured such that at the expiration of a five-minute time interval in the READY state 832 state transition 838 from the READY state 832 to the OFF state 824 is effected.

According to one embodiment of the invention, when the system enters the run state 842, if a lamp-restart timer is nonzero then the system immediately transitions 844 to restart-wait state 846. Otherwise, the lamp turns on and the current timing value of a "lamp-on timer" 848 is displayed in minutes and seconds on the liquid crystal display 402. For example, a time of 15 minutes is shown as "15:00." This value immediately begins counting (down toward 0 in one second increments.

According to one embodiment of the invention, when the lamp-on timer reaches three minutes (3:00) a first tone having a duration of approximately one-half second is emitted by the speaker 450, if such a system is used. According to another embodiment of the invention, when the lamp-on timer reaches each of three 3 seconds remaining, two (2) seconds remaining and one (1) second remaining, a second tone having a duration of approximately one-half (½) second is emitted by the speaker 450. In like fashion, when the lamp-on timer times out to zero, a third tone is emitted by the speaker. In one embodiment of the invention, the third tone has a duration of about two (2) seconds is emitted by the speaker. According to one embodiment of the invention, the first, second and third tones are of different frequencies respectively.

As discussed above, in relation to FIG. 4, the four LED indicators 430, 432, 434 and 436 serve to indicate status of the lamp-on timer. According to a specific embodiment of the invention, indicator 430 is illuminated during a time interval when the timer value is between 15:00 and 0:00; indicator 428 is off between a timer value of 15:00 and a timer value of 11:16, and is illuminated from 11:15 to 0:00; indicator 426 is off between a timer value of 15:00 and a timer value of 7:31, and is illuminated from 7:30 to 0:00; and indicator 424 is off between a timer value of 15:00 and a timer value of 3:46, and is illuminated from 3:45 to 0:00.

According to one embodiment of the invention, the key input (corresponding to presence of a light guide 120 and associated integrated circuit memory device 326) is polled periodically while the system is in run state 842. If the key input is found to be stably inactive, the system sets the lamp restart timer to 10 seconds and executes transition 850 to key state 818.

According to one embodiment of the invention, pressing the off button 422 while the system is in run state 842 causes the lamp restart timer to be set to 10 seconds and also executes transition 850 to key state 818.

According to still another embodiment of the invention, depressing pause button 426 while the system is in run state 842 causes the system to set the lamp restart timer to 10 seconds and execute state transition 852 into pause state 854. Pressing the start button 424 while in run state 842, however, has no effect on the system and causes no state transition. Likewise, pressing the on button 420 while the system is in run state 842 has no effect on the system and causes no state transition.

According to one embodiment of the invention, while the system is in restart wait state 846, the light source 200 remains off. Likewise, the LEDs 428, 430, 432, 434 and 436 also remain off.

The display 402 shows "WAIT-XX" and begins to countdown at a rate of one count per second. XX is the remaining time in seconds on the lamp restart timer.

According to one embodiment of the invention, while the system is in restart wait state 846 the key input is polled and if a stable inactive state is detected, transition 860 to key state 818 is effected.

Pressing the off button 422 causes the system to transition from the restart wait state 846 into OFF state 824. Pressing the start button 424 has no effect and causes no state transition. Likewise, pressing the on button 420 causes no state transition and has no effect on the system. Pressing the pause button 426 causes the system to transition from reset wait state 846 to pause state 854. According to one embodiment of the invention, when the system is in the restart wait state 846 and the lamp restart timer decrements to zero, the system transitions 862 into the run state 842.

In the pause state 854, the light source 200 is off. The lamp on timer is suspended. Its value in minutes and seconds is shown blinking on the LCD device 402. The LEDs remain in the condition according to the paused timer value as discussed above. The key input is sampled, and a stable inactive state is detected. The system transitions from the pause state 854 to the key state 818.

According to one embodiment of the invention, pressing the off button 422 while in the pause state 854 causes a transition to the key state 818. Pressing the pause button 426 or the start button 424 causes a transition from the pause state 854 to the run state 842. Pressing the on button 420 has no effect while in the pause state.

According to one embodiment of the invention, a timer 866 is executed while in the pause state 854. In one embodiment, when the timer 866 reaches a time value of fifteen (15) minutes, the system transitions from the pause state 854 to the key state 818.

In various embodiments, the system includes special operations modes for use in testing and analysis of system status. Among these special operations modes is an accelerated time mode. Accelerated time mode is identical to normal mode operation, except that several timing values are shortened to facilitate functional testing of hardware and firmware. One of skill in the art would readily understand this function and be able to establish appropriate shortened timing values.

According to one embodiment of the invention, accelerated time mode is initiated by simultaneously depressing buttons 420, 422, 424 and 426. In one embodiment of the invention, the buttons are depressed until the LCD display device 402 displays the message "ZOOM2." In one embodiment of the invention, an accelerated run time is approximately thirty (30) seconds; a run warning tone is fifteen (15) seconds, a ready state maximum duration is two (2) minutes, a paused state maximum duration is two (2) minutes to and LEDs minimum illumination intervals are five (5) seconds.

In operation, the lamp system 100 is positioned with respect to the patient in a dental chair (not shown). Once the lamp system 100 is positioned with respect to the patient, the operator aligns the light guide 106 with a retracting device in the patient's mouth. The light guide 106 may be set to a wide range of positions through the wide range of motion of both the boom 108 with respect to the mast 110 and the lamp head 102 with respect to the boom 108. The light guide 106 is shaped and configured to mate with lip retracting devices (not shown) worn by the patient thereby providing a substantially precise alignment with the patient's mouth. This alignment will remain during operation, even allowing for slight movement of the patient's head. This is possible because the retracting device is removably engaged with the light guide, and is positioned but not fixed to allow for this slight movement of the patient's head, as note above.

The embodiments and materials are exemplified as is described in U.S. Application No. 60/604,577, "Lip Retractors", filed Aug. 25, 2004.

Figure 9:
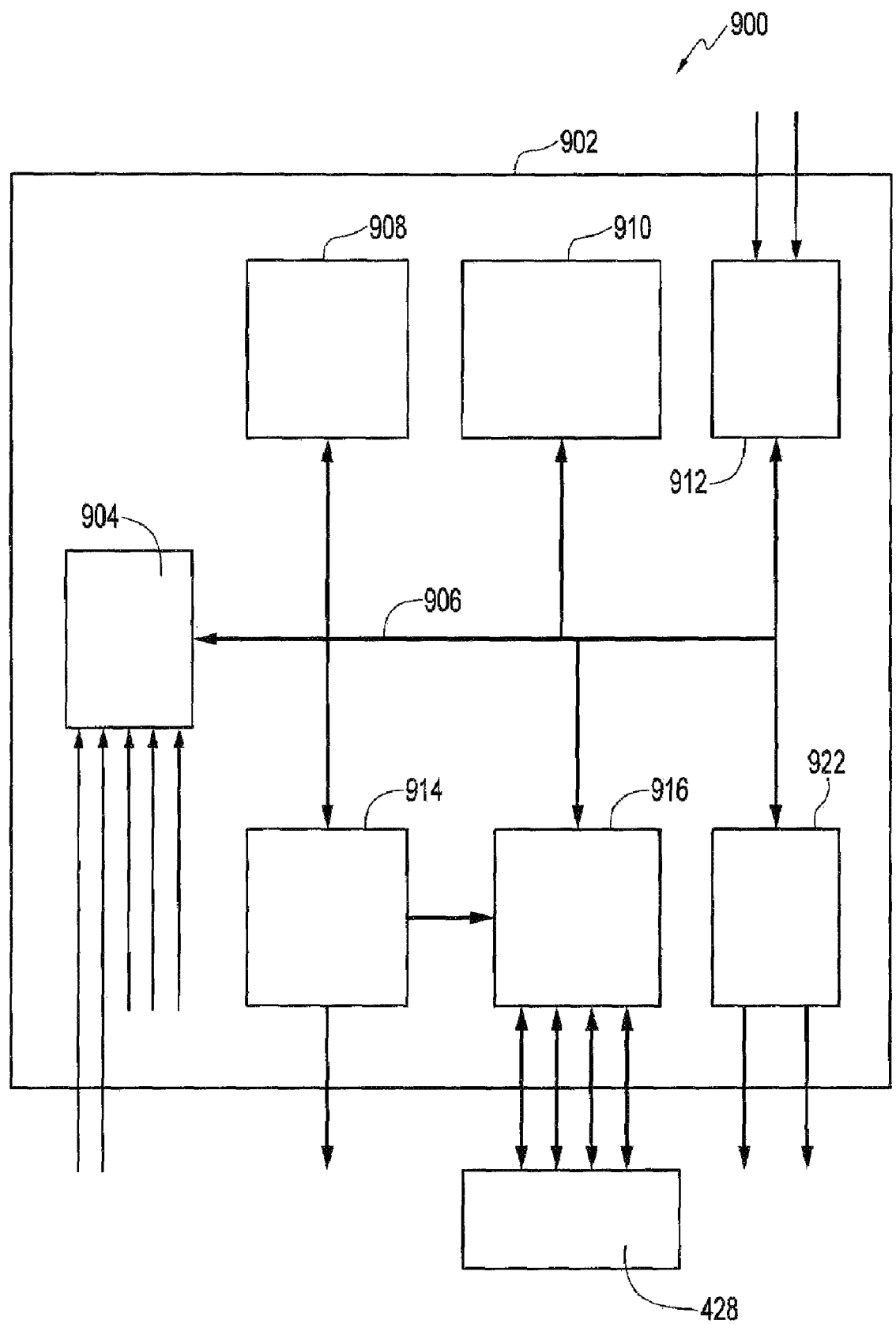
FIG. 9 shows a block diagram of a control system according to another embodiment of the invention.

FIG. 9 shows another embodiment of the invention, in which dental lamp control is performed by a control system 900 including a microcontroller. One microcontroller that is well-known in the art, is the Intel MCS-8051 microcontroller. Accordingly, in the embodiment of control system 900 shown in FIG. 9, an Intel MCS-8051 902 is employed. As illustrated, microcontroller 902 includes a central processing unit 904 that is coupled to a system bus 906. The system bus 906 is also coupled to a program memory device 908. In addition, the system bus 906 is coupled to a data memory device 910 and two timer/counter devices 912. The system bus 906 is further coupled to an expansion bus controller 914, and to a programmable I/O port 916. A programmable serial port is also coupled to the system bus 906. In the illustrated embodiment, the expansion bus control device 914 is coupled directly to the programmable I/O device 916 for control thereof. According to one embodiment, the programmable I/O device 916 is also coupled to a demultiplexer 429, such as that previously discussed in relation to FIG. 4 above. Other aspects of the microcontroller 900 include an oscillator and timing device and a serial port device 922.

According to an illustrated embodiment, the control system 900 is programmed by recording an operational program in program memory 908. According to one embodiment of the invention, the operational program includes a plurality of statements adapted to effect the state machine function illustrated in FIG. 8, above.

Figure 10:
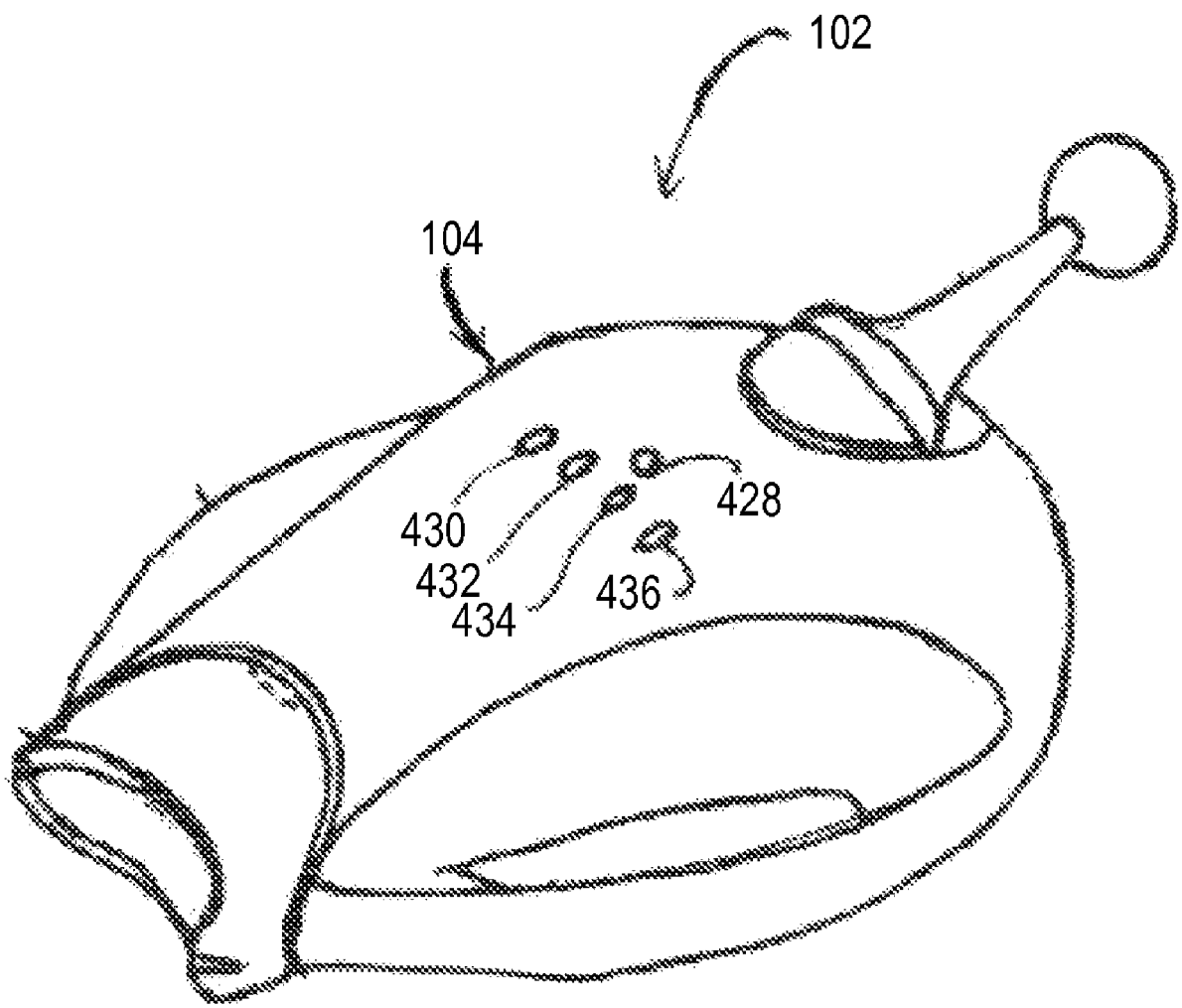
FIG. 10 shows a lamp head of a dental lamp, in perspective view, according to one of one end of the invention.

FIG. 10 is a perspective view of a lamp head 102 according to one embodiment of the invention. The lamp head 102 includes the lamp head housing 104.

The lamp head housing 104 includes lighted indicators 428, 430, 432, 434 and 436, as discussed above in relation to FIG. 4. In an alternative embodiment of the invention, the lamp head housing 104 includes an indicator system in which a lighted indicator blinks at selected intervals to indicate the percentage of the whitening process that has been completed. In another alternative embodiment of the invention, a display mounted in the lamp head housing 104, such as a liquid crystal display, indicates the status of the whitening process.

According to one embodiment, the light sources for the indicators, such as, LEDs, may be disposed inside protrusions through the surface of the lamp head housing 104. The protrusions may be sealed. In a second alternative embodiment, the top surface of the lamp head housing 104 may be smooth and the LEDs are positioned in recesses in the undersurface of the lamp head housing 104. This embodiment has the advantage that the surface of the lamp head housing 104 is easier to clean and also does not collect debris as would occur if there were protrusions in the lamp head housing surface. In a third alternative embodiment, the lamp head housing surface has markings positioned over the lighted indicators of the second embodiment.

According to one embodiment of the invention, the boom 108 is essentially a hollow tube and contains I/O cables. The I/O cables include an electrical plug that is received by the electrical connector in the lamp head housing 140 thereby removably attaching the lamp head 102 to the boom electronically. The I/O cables provide power to the lamp head 102 and also carry data to and from the power pack 122.

In operation, the light guide 120 is attached to the lamp head housing 140. The light guide 120 has both a mechanical attachment mechanism and an electrical contact 606 between the light guide memory integrated circuit 326 and electronics in the lamp head housing 140. The electrical contact 606 mates with a plug in the lamp head forming an electromechanical connection that enables signaling between the light guide memory integrated circuit 326 and electronics in the lamp head housing 140.

The light guide 120 is aligned with the patient's mouth using a lip retracting device, and the positionability of the lamp system 100 when the whitening treatment is administered, for example. A signaling device within lamp head 102, or within the power pack, records, for example, an analog to the duration of use of light guide onto the memory integrated circuit 326. When a light guide usage limit is reached, the controller 300 precludes activation of the light source 200 in the lamp head housing 140 and the light guide 120 is replaced in order to operate the lamp system 100.

According to various embodiments of the invention, the memory integrated circuit 326 may communicate with the controller 300 through infrared radiation or through wireless radio signals or through light from the visible portion of the electromagnetic spectrum.

Figure 11:
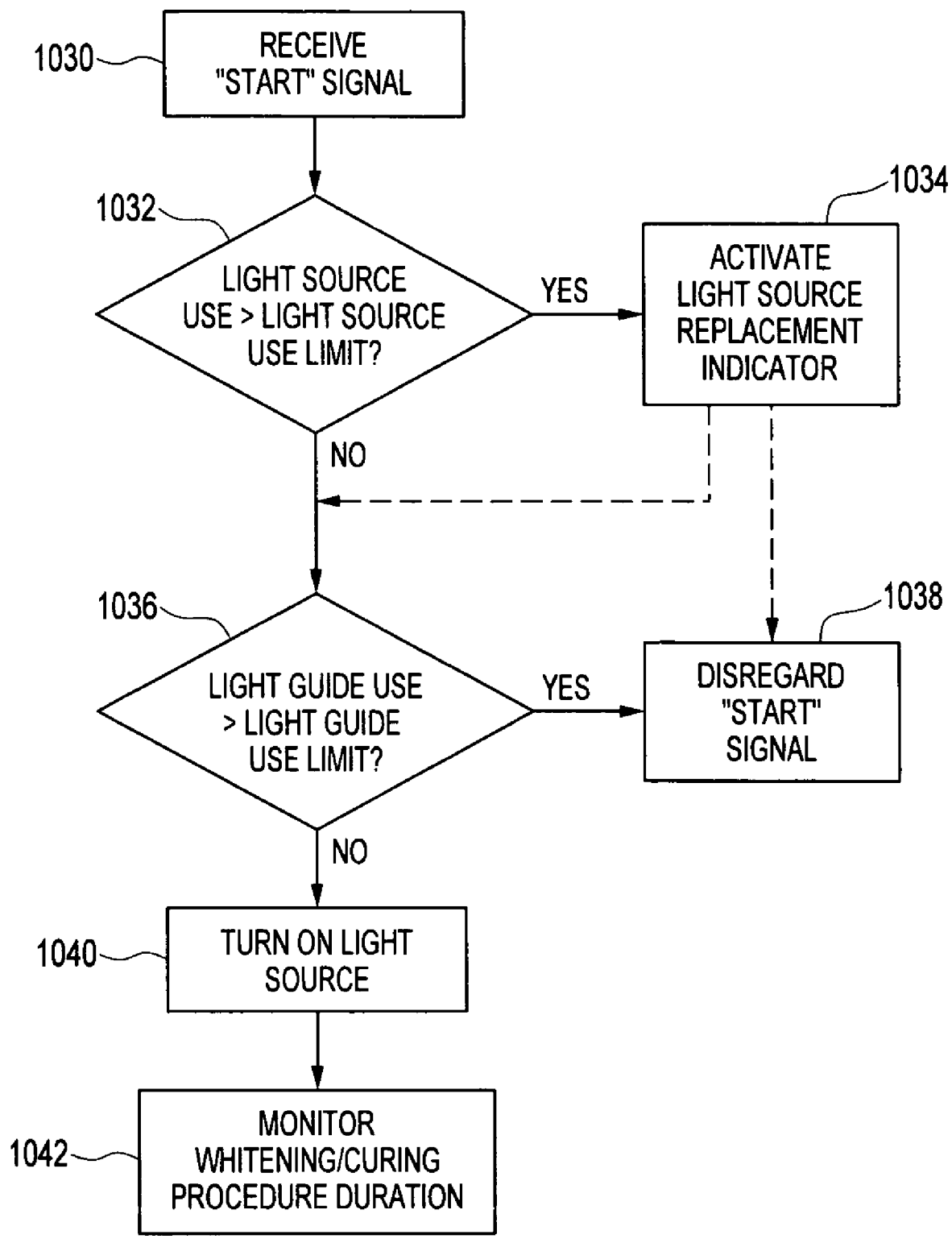
FIG. 11 shows a flowchart illustrating operation of a control system according to one embodiment of the invention.

FIG. 11 is a flow chart showing one embodiment of the start process of the lamp system that is executed by the control system 300.

At step 1030, the control system 300 receives a "start" signal from the lamp controls 300. The "start" signal activates an initializing process that includes determining whether the light source 200 and light guide have reached their usage limits. The control system 300 stores a light source usage limit, a light guide usage limit, and a whitening/curing procedure time limit that is divided into preselected time periods.

At step 1032, the control system 300 checks whether the light source 200 has been used longer than the light source usage limit stored in the control system 300. The light source usage limit is, for example, 100 hours. The control system 300 monitors the time that the source 200 is on and adds this value to the amount of time accumulated from previous treatment procedures, if any. When the "start" signal is received from the lamp control 300, the control system 300 compares the accumulated light source on time with the light source usage limit. If the light source usage limit has been exceeded, the control system 300 proceeds to step 1034. If the light source usage limit has not been exceeded, the control system 300 proceeds to step 1036.

At step 1034, the control system 300 activates the light source replacement indicator 152 in the lamp head 102. In a first embodiment of the control system 300, the control system continues with the process of starting the lamp system 100. In this embodiment, the control system 300 proceeds to step 1036. In a second embodiment of the control system 300, the control system 300 does not allow the lamp to be turned on. In this embodiment, the control system 300 proceeds to step 1038. In either embodiment, the control system 300 is reset when the light source 200 is replaced.

At step 1036, the control system 300 determines whether the light guide usage has exceeded the light guide usage limit stored in the control system 300. The light guide usage limit is typically the amount of time of, for example, a single whitening or curing treatment. The light guide usage limit is, for example about 30 minutes to about 90 minutes or, sixty minutes. The control system 300, as mentioned above in step 1032, monitors the time that the light source 200 is on. The control system 300 writes the amount of time that the light source 200 has been on since the beginning of a treatment procedure to a recording device on the light guide 106. The recording device is, for example, a memory integrated circuit 246. When the "start" signal is received from the lamp controls 300, the control system 300 compares the light source "on" time stored on the recording device in the light guide 106 with the light guide usage limit stored by the control system 300. If the light guide usage limit has been exceeded, the control system 300 proceeds to step 1038. If the light guide usage limit has not been exceeded, the control system 300 proceeds to step 1040.

At step 1038, the control system 300 disregards the "start" signal with regard to turning the light source 200 on. That is, the control system 300 does not allow the lamp system 100 to operate if the light guide lifetime has expired. This portion of the control system 300 acts to prevent the light guide from being reused. The light guide 106 is intended to be a single-use device to be discarded after each whitening or curing treatment.

At step 1040, the control system 300 starts the lamp (i.e. turns on the light source 200).

At step 1042, the control system 300 monitors the whitening or curing treatment procedure time. In this step, the control system 300 monitors the time that the light source 200 is on. The monitoring procedure of the control system 300 is described below with regard to FIG. 12.

Figure 12:
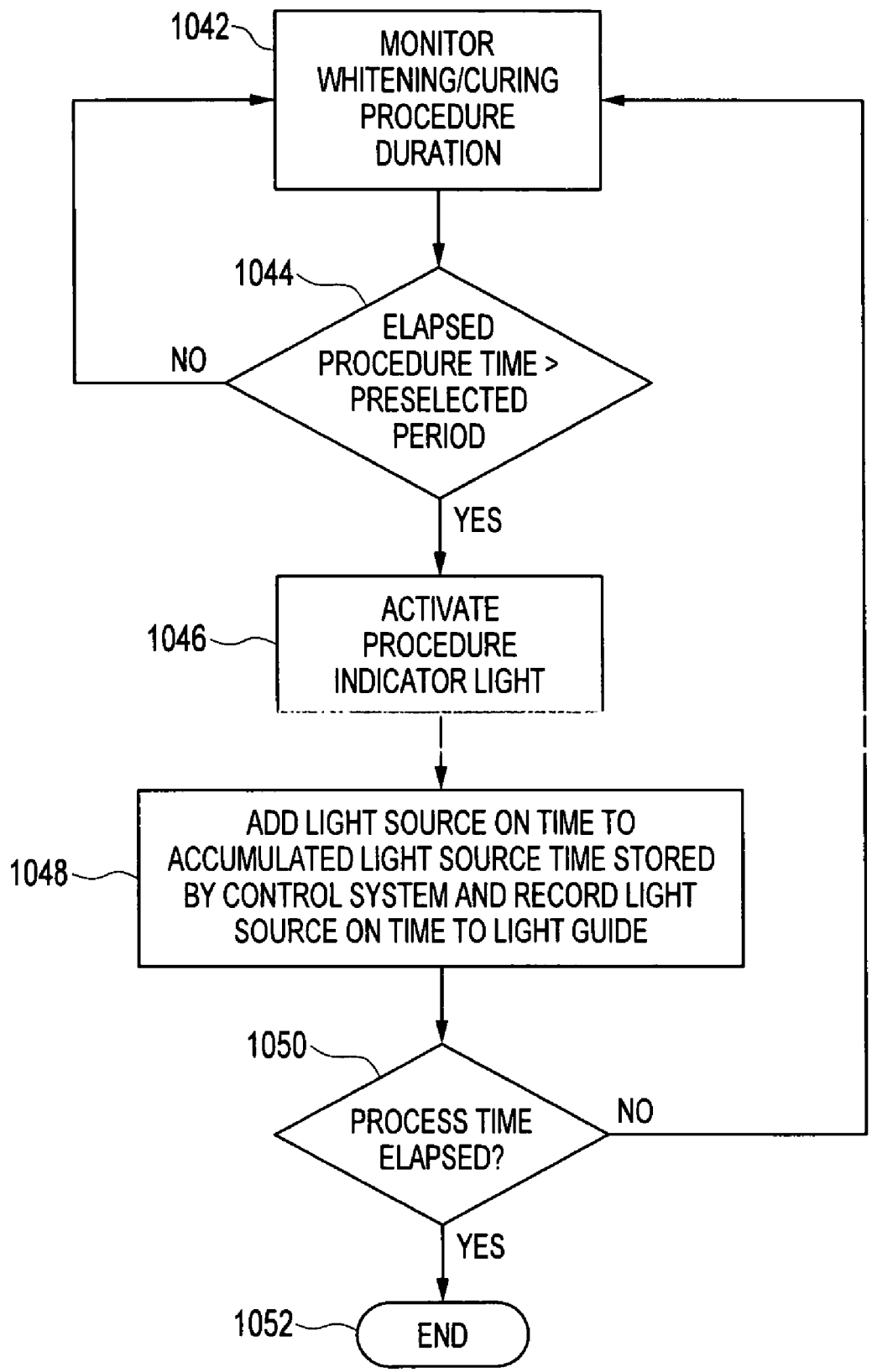
FIG. 12 shows a flowchart illustrating operation of a control system according to one embodiment of the invention.

FIG. 12 is a flow chart showing one embodiment of the monitoring process of the lamp system that is executed by the control system 300.

At step 1042, the control system 300 monitors the duration of the whitening or curing treatment, that is, the control system 300 monitors the light source "on" time.

At step 1044, the control system 300 determines whether the elapsed procedure time has exceeded a preselected time period. Here, the preselected time period is some portion of the overall treatment time such as one quarter of the total treatment time. If the elapsed procedure time has not exceeded the preselected time period, the control system 300 continues to monitor the treatment duration (step 1042). If the elapsed procedure time does exceed the preselected time period, then the control system 300 proceeds to step 1046.

At step 1046, the control system 300 activates a procedure indicator light, for example one of the lighted indicators 150 described above with regard to FIG. 6, or a voice alert, as noted above. In one embodiment, the control system 300 activates another lighted indicator 150 as each treatment portion time elapses so that if, for example, there are four lighted indicators, all four are lit at the end of the treatment procedure. In another embodiment, there is a single lighted indicator to indicate the time progression of the treatment. In this embodiment, the light indicator has varying flash rates to indicate the how much time has elapsed since the start of treatment. The control system 300 then proceeds to step 1048. In yet another embodiment, a voice alert system is used to alert the dental professional of the progress of the treatment.

At step 1048, the control system 300 adds the time that the light source has been on to the accumulated time that the control system 300 has stored from previous treatment procedures, if any. The control system 300 also writes the time that the light source has been on to the light guide recording device, such as the memory integrated circuit 246. The control system 300 then proceeds to step 1050.

At step 1050, the control system 300 determines whether the overall process time has elapsed. The overall process time is the time duration of the whitening or curing treatment. If the overall process time has not elapsed, the control system 300 returns to step 1042, monitoring the whitening/curing duration. If the overall process time has elapsed, the control system 300 proceeds to step 1052.

At step 1052, the duration of the whitening/curing treatment has elapsed and the control system 300 turns off the light source 200. In one embodiment of the invention, the controller allows the light source 200 to remain on for a limited time longer when a time limit of a light guide expires during the course a treatment. In a further embodiment of the invention, the controller allows the light source 200 to be illuminated whether or not its design lifetime has been exceeded.

While preferred embodiments of the invention have been described and illustrated above, it should be understood that these are exemplary of the invention and are not to be considered as limiting. Accordingly, the invention is not to be considered as limited by the foregoing description, but is only limited by the scope of the claims appended hereto.

The invention claimed is:

1. A method of controlling a lamp for dentistry applications comprising:
   producing a timing signal;
   receiving said timing signal at a recordable medium;
   altering said recordable medium in response to said receiving said timing signal to produce an altered recordable medium; and
   evaluating said altered recordable medium to determine a state of a consumable product; and
   controlling an illumination state of said lamp according to said state of said consumable product; wherein said lamp is in a non-illuminated state when said state of said consumable product is in the state when said consumable product has previously been used for at least about 30 to about 90 minutes.

2. The method of claim 1 further comprising controlling an illumination state of said lamp according to said state of said consumable product.

3. The method of claim 2 wherein said controlling said illumination state of said lamp comprises maintaining said lamp in a non-illuminated state when said state of said consumable product includes an expired state of said consumable product.

4. The method of claim 3 wherein said expired state of said consumable product includes a state of said consumable product in which said consumable product has previously been used for at least about a particular time duration.

5. The method of claim 4 wherein said particular time duration comprises at least about 30 to about 90 minutes.

6. The method of claim 3 wherein said consumable product comprises a dental light guide.

7. The method of claim 3 wherein said altering said recordable medium comprises writing a data signal to a memory integrated circuit.

8. The method of claim 7 wherein said writing a data signal to a memory integrated circuit comprises periodically changing a state of a memory element of said memory integrated circuit from a first binary state to a second binary state.

9. The method of claim 2 wherein said producing a timing signal comprises changing a voltage of electrical conductor in response to a program signal received at central processing unit from a program storage memory device.

10. The method of claim 2 further comprising sending a signal to a user interface device; and activating said user interface device to indicate said state of said consumable product.

11. A method of controlling illumination of a dental lamp system for dental applications, comprising:
   recording on a recording medium a data signal indicating a duration of use of a component of the dental lamp system; and
   employing a timing device to read said recorded data signal from said recordable medium for controlling whether to activate a light source of said dental lamp system after the component of the dental lamp is coupled to the dental lamp system.

12. The method of claim 11 wherein said timing device includes an integrated circuit microprocessor device.

13. The method of claim 12 wherein said microprocessor device comprises a general-purpose microprocessor device or a specialized microcontroller device.

14. The method of claim 11 wherein said recordable medium comprises an integrated circuit memory device.

15. The method of claim 14 wherein said integrated circuit memory device comprises a flash memory device, a resistive memory device, a magneto-resistive memory device, a static CMOS memory device coupled to a power source or combinations thereof.

16. The method of claim 11 wherein said timing device inhibits illumination of said light source when said recorded data signal indicates that said duration of use of said component of said lamp system exceeds a particular time interval.

17. The apparatus of claim 11 wherein said recorded data signal comprises a plurality of digital "one's" recorded on said recordable medium.

18. The apparatus of claim 11 wherein said timing device controls activation of said light source by sending a logical signal to a switching device, said switching device being coupled to a source of power for the light source and to said light source.

19. The apparatus of claim 11 wherein said timing device produces said recorded data signal and transmits said recorded data signal to said recordable medium for recording on said recordable medium.

20. The apparatus of controlling illumination of a dental lamp system for dental applications, comprising:
   recording on a recording medium a data signal indicating a duration of use of a component of the dental lamp system; and
   employing a timing device to read said recorded data signal from said recordable medium for controlling illumination of a light source of said dental lamp system; wherein said timing device inhibits illumination of said light source when said recorded data signal indicates that said duration of use of said component of said lamp system exceeds a particular time interval, said time interval is between about 30 minutes to about 90 minutes.

21. The apparatus of claim 16 wherein said component of said lamp system comprises a light guide.

22. The apparatus of claim 20 wherein said component of said lamp system comprises a light guide.

23. The apparatus of claim 22 further comprising replacing said light guide when the duration of use exceeds the particular time interval.

24. The apparatus of claim 20 wherein said timing device controls activation of said light source by sending a logical signal to a switching device, said switching device being coupled to a source of power for the light source and to said light source.

25. The apparatus of claim 20 wherein said timing device produces said recorded data signal and transmits said recorded data signal to said recordable medium for recording on said recordable medium.

* * * * *